(12) United States Patent
Kelly et al.

(10) Patent No.: US 10,525,463 B2
(45) Date of Patent: *Jan. 7, 2020

(54) INTEGRATED TESTING DEVICE

(71) Applicant: ATOMO DIAGNOSTICS PTY LIMITED, Drummoyne, NSW (AU)

(72) Inventors: John Michael Kelly, Newington (AU); Eric Siu, Newington (AU); Alison Ruth Norcott, Newington (AU); Christopher David Dunn, Newington (AU); Ian Frederick Johnson, Newington (AU); Ernesto Monis Hueso, Newington (AU); Richard Sokolov, Newington (AU)

(73) Assignee: ATOMO DIAGNOSTICS PTY LIMITED, Drummoyne, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/083,839

(22) Filed: Mar. 29, 2016

(65) Prior Publication Data

US 2017/0001192 A1     Jan. 5, 2017

Related U.S. Application Data

(63) Continuation of application No. 13/838,145, filed as application No. PCT/AU2011/000315 on Mar. 18, (Continued)

(30) Foreign Application Priority Data

Mar. 19, 2010    (AU) ................................ 2010901175
Oct. 15, 2010    (AU) ................................ 2010904615

(51) Int. Cl.
*B01L 3/00*      (2006.01)
*A61B 5/15*      (2006.01)
(Continued)

(52) U.S. Cl.
CPC ............ *B01L 3/5023* (2013.01); *A61B 5/145* (2013.01); *A61B 5/1411* (2013.01); *A61B 5/151* (2013.01);
(Continued)

(58) Field of Classification Search
CPC ................. B01L 2200/16; B01L 3/502; B01L 3/502715; A61B 5/1411; A61B 5/14532;
(Continued)

(56) References Cited

U.S. PATENT DOCUMENTS

| | | |
|---|---|---|
| 4,637,403 A | 1/1987 | Garcia et al. |
| 4,661,319 A | 4/1987 | Lape |

(Continued)

FOREIGN PATENT DOCUMENTS

| | | |
|---|---|---|
| CN | 101641052 | 1/2013 |
| EP | 1284121 | 2/2003 |

(Continued)

OTHER PUBLICATIONS

International Search Report dated Dec. 20, 2011 in International Application No. PCT/AU2011/001321, International Filing Date Oct. 17, 2011. (4 pages).

(Continued)

*Primary Examiner* — Sally A Merkling
(74) *Attorney, Agent, or Firm* — Shutts & Bowen LLP

(57) ABSTRACT

An integrated testing device and method are disclosed. The device includes an integral reservoir for a test fluid, and an actuator, so that the test fluid can be dispensed to facilitate the test.

11 Claims, 18 Drawing Sheets

Related U.S. Application Data 2011, now Pat. No. 9,295,987, said application No. 13/838,145 is a continuation of application No. 13/635,903, filed as application No. PCT/AU2011/000315 on Mar. 18, 2011, said application No. 13/838,145 is a continuation of application No. PCT/AU2011/001321, filed on Oct. 17, 2011.

(51) Int. Cl.
    *A61B 5/151*     (2006.01)
    *A61B 5/157*     (2006.01)
    *A61B 5/145*     (2006.01)

(52) U.S. Cl.
CPC ........ *A61B 5/157* (2013.01); *A61B 5/150022* (2013.01); *A61B 5/15111* (2013.01); *A61B 5/15113* (2013.01); *A61B 5/15117* (2013.01); *A61B 5/15144* (2013.01); *A61B 5/15186* (2013.01); *A61B 5/15192* (2013.01); *A61B 5/150305* (2013.01); *A61B 5/150343* (2013.01); *A61B 5/150358* (2013.01); *A61B 5/150412* (2013.01); *A61B 5/150503* (2013.01); *A61B 5/150549* (2013.01); *A61B 5/150618* (2013.01); *A61B 5/150717* (2013.01); *A61B 5/150755* (2013.01); *A61B 5/150824* (2013.01); *B01L 3/502* (2013.01); *A61B 5/14532* (2013.01); *A61B 2562/0295* (2013.01); *B01L 2200/0605* (2013.01); *B01L 2200/16* (2013.01); *B01L 2300/14* (2013.01); *B01L 2400/0475* (2013.01)

(58) Field of Classification Search
CPC .......... A61B 5/150358; A61B 5/15113; A61B 5/6833
See application file for complete search history.

(56) References Cited

U.S. PATENT DOCUMENTS

| | | | |
|---|---|---|---|
| 5,096,669 A | 3/1992 | Lauks et al. | |
| 5,249,584 A | 10/1993 | Karkar et al. | |
| 5,714,390 A | 2/1998 | Hallowitz et al. | |
| 6,264,619 B1 | 7/2001 | Ferguson | |
| 6,830,551 B1 | 12/2004 | Uchigaki et al. | |
| 7,885,697 B2 | 2/2011 | Brister et al. | |
| 7,946,984 B2 | 5/2011 | Brister et al. | |
| 8,229,534 B2 | 7/2012 | Brister et al. | |
| 2002/0002344 A1 | 1/2002 | Douglas et al. | |
| 2003/0013121 A1 | 1/2003 | Khan | |
| 2005/0283094 A1 | 12/2005 | Thym et al. | |
| 2007/0100213 A1 | 5/2007 | Dossas et al. | |
| 2008/0319347 A1* | 12/2008 | Keren | A61B 5/157 600/583 |
| 2010/0036282 A1 | 2/2010 | List et al. | |
| 2010/0184126 A1 | 7/2010 | Rutty et al. | |
| 2011/0105951 A1 | 5/2011 | Bernstein | |
| 2011/0144465 A1 | 6/2011 | Shults et al. | |
| 2011/0190614 A1 | 8/2011 | Brister et al. | |
| 2012/0283543 A1 | 11/2012 | Brauker et al. | |

FOREIGN PATENT DOCUMENTS

| | | |
|---|---|---|
| EP | 1374770 | 1/2004 |
| JP | 2012505639 | 3/2012 |
| JP | 5127839 | 1/2013 |
| WO | 1988000812 | 2/1988 |
| WO | 2001013795 | 3/2001 |
| WO | 2002078533 | 10/2002 |
| WO | 2004078232 | 9/2004 |
| WO | 2006037646 | 4/2006 |
| WO | 2008056363 | 5/2008 |
| WO | 2008085052 | 7/2008 |
| WO | 2008149333 | 12/2008 |
| WO | 2009147680 | 12/2009 |

OTHER PUBLICATIONS

International Preliminary Report on Patentability dated Jul. 30, 2012 in International Application No. PCT/AU2011/000315, International Filing Date Mar. 18, 2011. (12 pages).

International Search Report dated Jun. 14, 2011 in International Application No. PCT/AU2011/000315, International Filing Date Mar. 18, 2011. (7 pages).

Supplementary Partial European Search Report dated Jan. 31, 2014 in EP Application No. 11 75 5574. (7 pages).

* cited by examiner

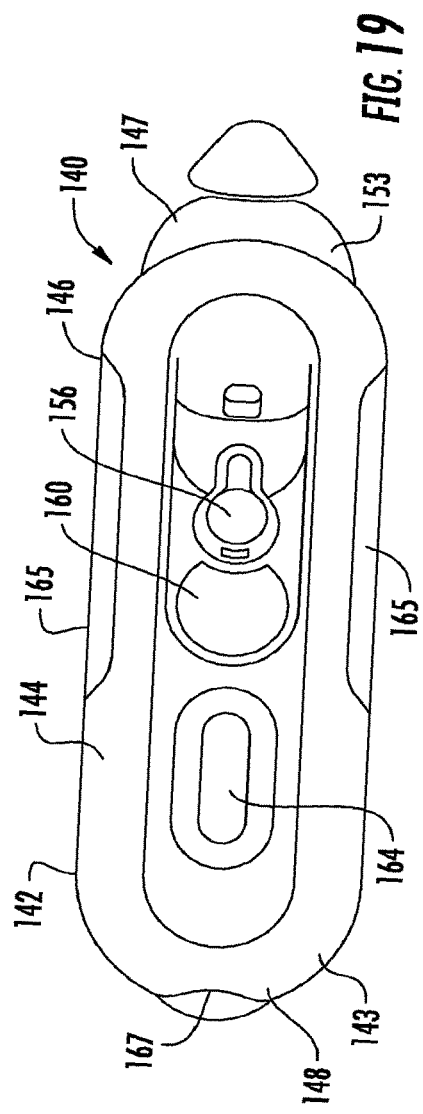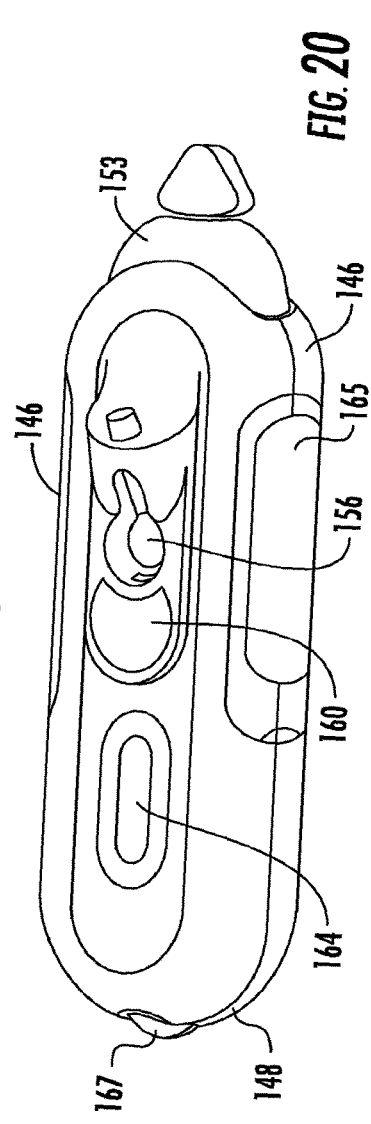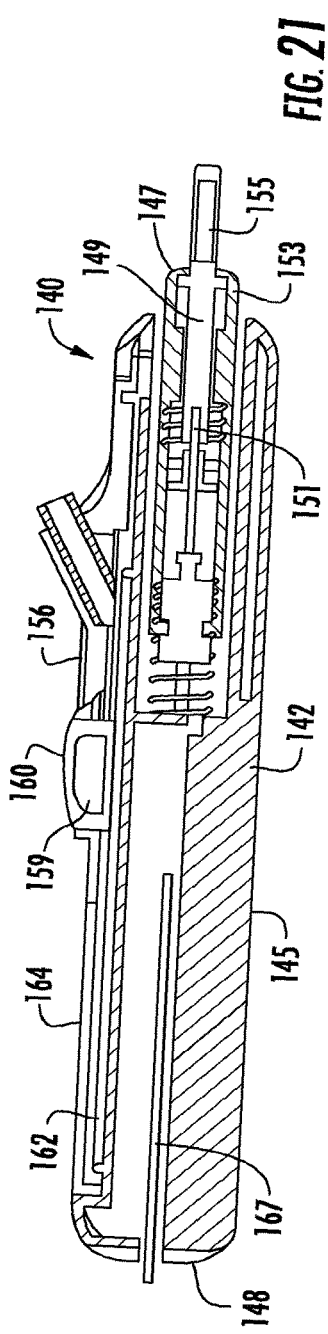

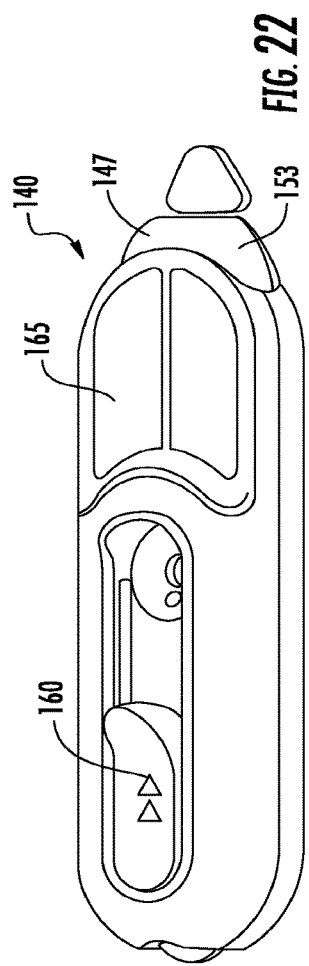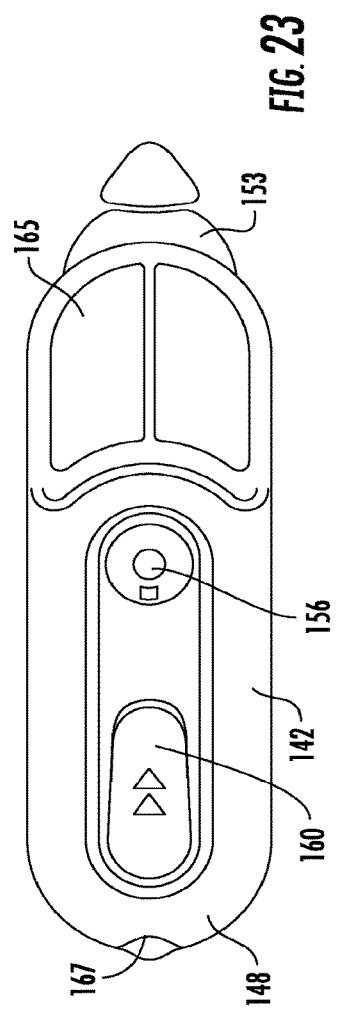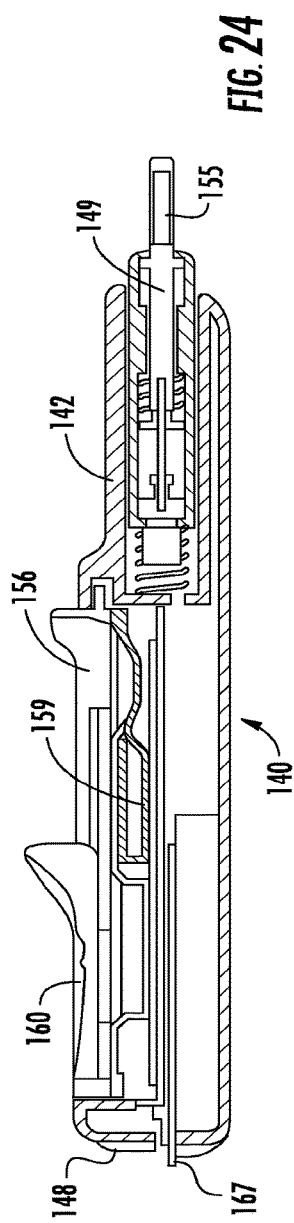

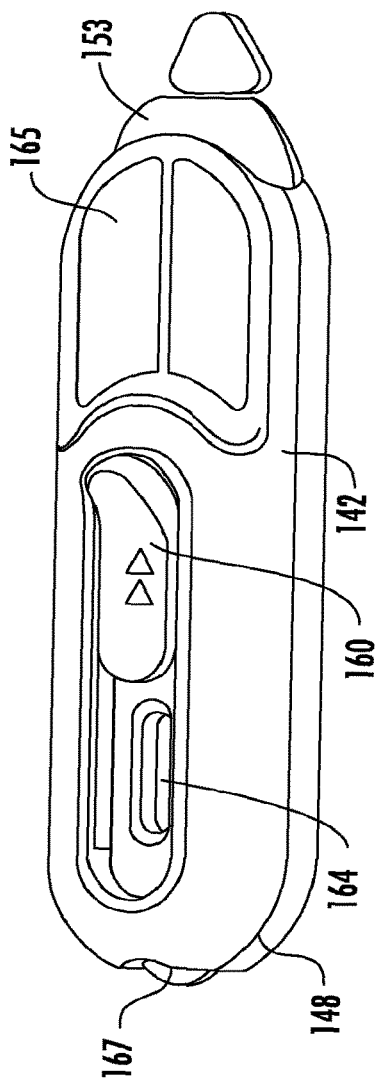
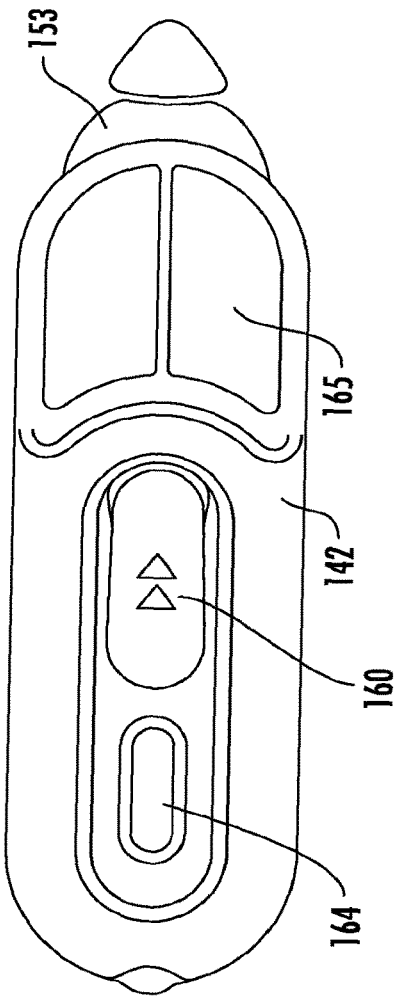

INTEGRATED TESTING DEVICE

TECHNICAL FIELD

The present invention relates to devices and methods for providing tests relating to bodily fluids such as blood, and particularly to the devices which facilitate such testing.

BACKGROUND OF THE INVENTION

Systems for performing relatively immediate tests, assays or diagnoses with relative ease are known. However, performing these relatively immediate tests, assays or diagnoses can require complicated instruction and multiple devices. The present invention is not concerned with the specific biochemical or chemical tests to be performed, but rather with the device and mechanical systems which house and contain the test strips or similar components. For example, the present invention may be applied with a lateral flow or similar type of rapid test.

In a typical conventional home or point of care test, for example, the user is presented with a collection of components, including the test device itself, a separate lancet, blood collection receptacles, a container of buffer or other test fluid, an adhesive bandage, cleaning wipes, and possibly further components. The user is expected to follow a very precise sequence of steps, typically including cleaning the site, operating the lancet, obtaining a blood sample and delivering it to the precise place required, applying a buffer solution at the right time and place and in the correct volume, and reading the test result and interpreting it.

Many tests are performed either as infrequent or one off procedures, so that the user does not become proficient through regular use. Procedures performed at point of care are carried out generally by skilled operators, but again specific tests may be performed infrequently. In such situations it would be advantageous if the test device could better facilitate simple, reliable and accurate operation.

It is an object of the present invention to provide a test device, which is capable of encouraging better compliance with at least some of the required test processes.

SUMMARY OF THE INVENTION

In a broad form, the present invention provides a test unit including an integrated reservoir for buffer or other test fluid. Upon operating an actuator, the fluid is dispensed so that it contacts the test component.

According to one aspect, the present invention provides an integrated testing device comprising:
 a test component;
 a reservoir adapted to contain a test fluid; and
 a fluid delivery actuator, wherein operation of the fluid delivery actuator causes the test fluid to be released from the reservoir so as to contact the test component.

According to another aspect, the present invention provides a method for conducting a test on a sample of a bodily fluid, comprising the steps of providing a testing device including a reservoir containing a test fluid, and further including a test component, wherein a sample of the bodily fluid is placed on the test component, and a quantity of test fluid is discharged from said reservoir onto the test component, the discharge being either before or after the sample is placed on the test component, so that the test component can thereby conduct the test.

According to a further aspect, the present invention provides an integrated testing device, comprising a support structure, a reservoir adapted to contain a test fluid, and a fluid delivery actuator, the device being adapted to receive a test component in said support structure, so that operatively, once a test component is received, the fluid delivery actuator can selectively cause the test fluid to be released from the reservoir so as to contact the test component.

Accordingly, implementations of the present invention allow for a test device to include a controlled volume of test fluid, such as a buffer, which can be dispensed within the test device itself, and to the correct site within the test device. This removes a significant source of potential error by a user, and increases the likely compliance with procedures and accuracy of the use of the test device.

BRIEF DESCRIPTION OF THE DRAWINGS

Preferred embodiments will now be described by way of example only, with reference to the accompanying drawings in which:

FIG. 19 shows a top view of a sixth embodiment of the present system;
FIG. 20 shows a perspective view of the embodiment of FIG. 19;
FIG. 21 shows a cross sectional view of the embodiment of FIG. 19;
FIG. 22 shows a perspective view of a seventh embodiment of the present system in a first position;
FIG. 23 shows a top view of the embodiment of FIG. 22;
FIG. 24 shows a cross sectional view of the embodiment of FIG. 22;
FIG. 25 shows a perspective view of the embodiment of FIG. 22 in a second position;
FIG. 26 shows a top view of the embodiment of FIG. 22 in a second position;

DETAILED DESCRIPTION OF THE INVENTION

Figure 1:
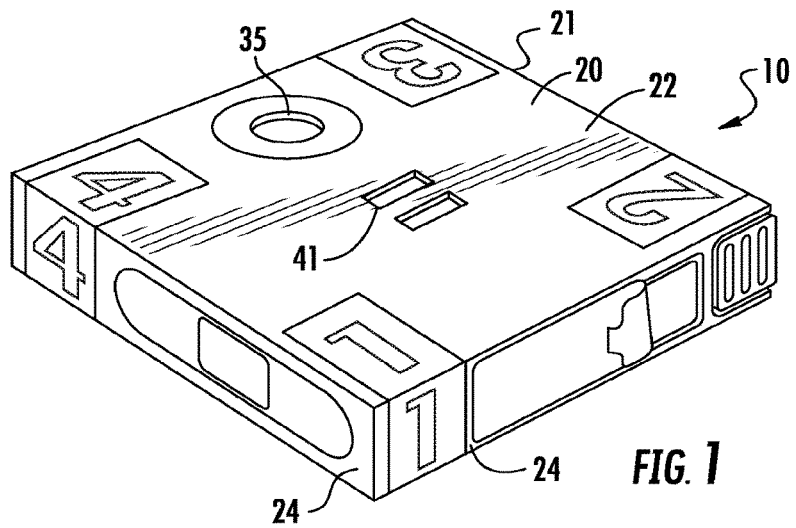
FIG. 1 shows an isometric view of one embodiment of the system.
Figure 2:
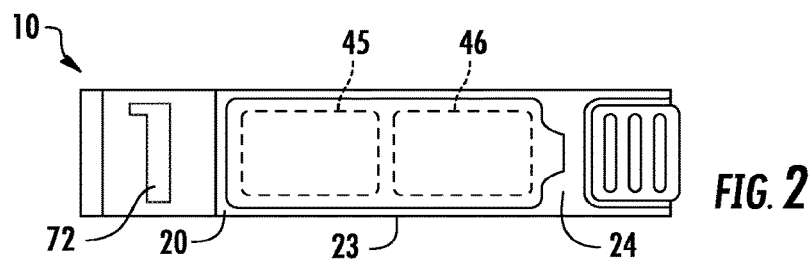
FIG. 2 shows a side view of the embodiment of FIG. 1.
Figure 3:
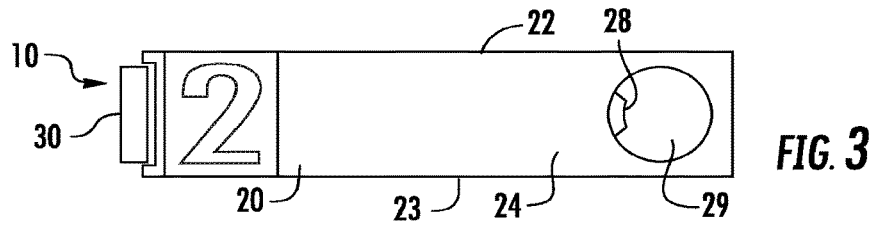
FIG. 3 shows a second side view of the embodiment of FIG. 1.
Figure 4:
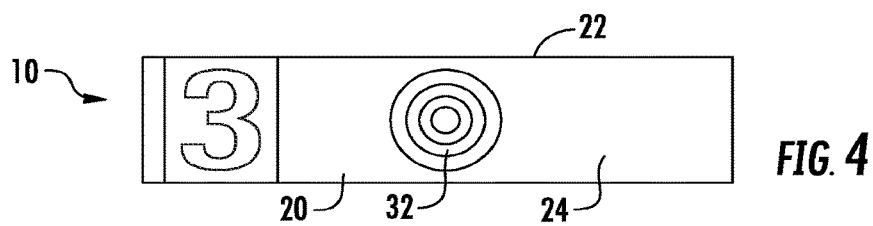
FIG. 4 shows a third side view of the embodiment of FIG. 1.
Figure 5:
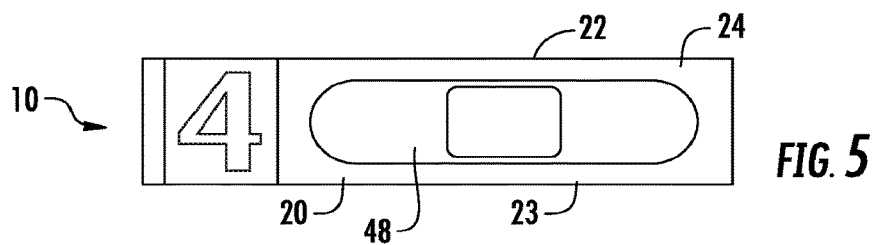
FIG. 5 shows a fourth side view of the embodiment of FIG. 1.

The present invention will be described with reference to a number of possible embodiments. It will be appreciated that the present invention is capable of being implemented in numerous ways, in addition to the examples provided. The embodiments are intended as illustrative, and are in no way limitative of the inventive concept or its possible implementations. Further, it will be understood that the features of different embodiments may be formed into different combinations, or added together, in order to provide further implementations of the present invention.

Referring to FIGS. 1 through 5, disclosed is a composite diagnostic system (10). The diagnostic system (10) comprises a support member (20) which is made up of a body (21) in the form of a housing having six sides. The body (21) comprises top face (22) bottom face (23) and sides (24).

Embodiments described are in a form which is sized to be hand-held by a user. However a person skilled in the art will be aware that the system may be designed for use on a table top or any alternative positioning and orientation and later embodiments are described for table top use.

The diagnostic system further comprises an integrated lancet (28). The integrated lancet is positioned in one side (24) of the body (21). The integrated lancet (28) is positioned such that a finger pad aperture (29) is adjacent the integrated lancet (28). The integrated lancet (28) comprises a lancet tip (not illustrated) which is moveable between a rest position in which the lancet is enclosed within the body (21) and an actuated position in which the lancet tip extends from the body. In the actuated position, the lancet tip extends from the body such that a finger positioned in the finger pad aperture is pierced by the lancet upon the lancet moving between the rest position and the actuated position.

In use, activation of the lancet between the rest position and the actuated position occurs through depression of a lancet activator (30) which is positioned on the body. Contact with the lancet activator (30) moves the lancet tip into the finger pad aperture (29) to pierce a finger or alternative body part positioned in that aperture.

Upon a user's finger being pierced by the lancet, the user or clinician moves the user's finger over the blood collection window (32) and bodily fluid, in this case blood, is collected at fluid collection window (32). The fluid collection window (32) is positioned proximal to the aperture (29) to allow a user to easily move the pierced finger between the aperture (29) and the fluid collection window (32) without depositing fluid other than in the window.

The diagnostic system further comprises a physiologically acceptable solution such as a buffer for supporting the blood or other bodily fluid. A solution delivery actuator (35) is positioned on the diagnostic system. Contact with the solution delivery actuator releases the buffer solution from an internal reservoir and delivers it to a test material incorporated into the diagnostic system (10). The test material may comprise a lateral flow test strip, a vertical flow test strip, solid phase test material, agglutination test material, a cartridge or reagent tube or any element which incorporates a reagent adapted to be mixed with the bodily fluid, a card incorporating a fluid sample retention material, an assay, a test strip or an integrated electrical circuit or any material adapted for retaining a sample and allowing a diagnostic test to be performed thereon.

The present invention is not principally concerned with precisely the nature of the test itself, but with the mechanical structures and components which allow an effective and accurate test to be made. Accordingly, any kind of chemical, biochemical, microbiological, genetic, biological or other test may be performed using implementations of the present invention, suitably modified to meet to the particular requirements of those tests. Whilst many of the examples are concerned with test strips, it will be understood that this is merely conventional and any form or shape of test component may be used. The term test component is to be accordingly understood in the broadest sense.

Similarly, whilst the examples are principally in the context of blood, any other fluid or other sample, for example urine, seminal fluid, plasma, wound discharges, or other materials could be utilised in testing according to the present invention.

The diagnostic system further includes a results window (41) which is positioned for easy viewing of the results of any diagnostic test performed.

An alcohol swab locator (45) in the form of a depression in which alcohol swabs and dry wipes can be inserted is positioned in side (24). The depression (45) is covered by a seal (46) such as a foil seal or plastic seal.

An adhesive bandage locator (48) is positioned in a further side of the diagnostic system. The adhesive bandage locator, is in a form of a depression which fits adhesive bandages such as Band-Aids™

The sides of the diagnostic system (10) are labelled with indicia (72) indicating the order in which the sides are to be used. This simplifies the process of utilizing the system and allows an at home user to confidently proceed through the necessary steps. The positioning of the finger pad aperture (29), the fluid collection window (32), the solution delivery actuator (35) the alcohol swab locator (45) and the adhesive bandage locator (48) allow for a simple movement through the steps of the process. This allows for an intuitive movement about the surfaces of the system (10). Thus the lancet activator (30) is adjacent the fluid collection window (32) which is adjacent the solution delivery actuator (35) which is positioned adjacent the adhesive Band-Aid™ locator (48) allowing for sequential motion about the system (10) when following the steps in the order indicated by the indicia (72).

Figure 6:
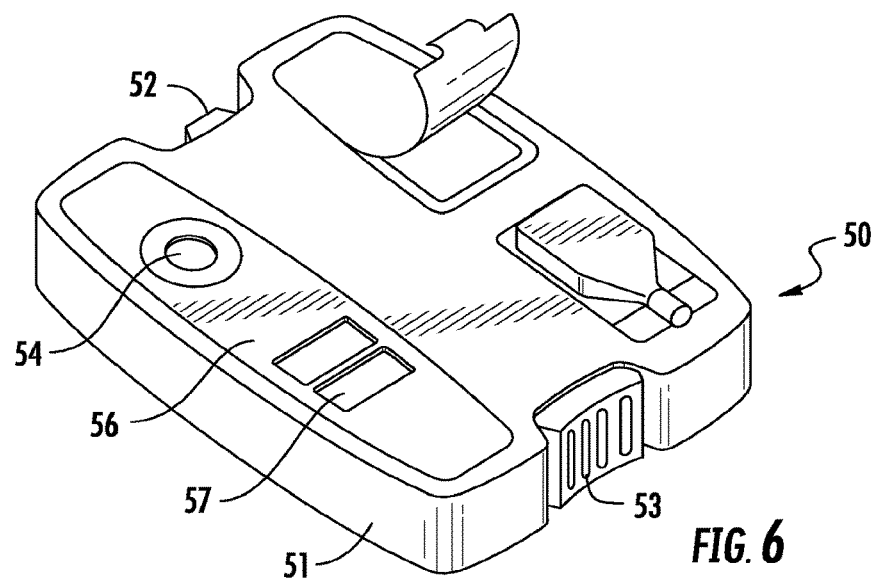
FIG. 6 shows an isometric view of a second embodiment of the present system.
Figure 7:
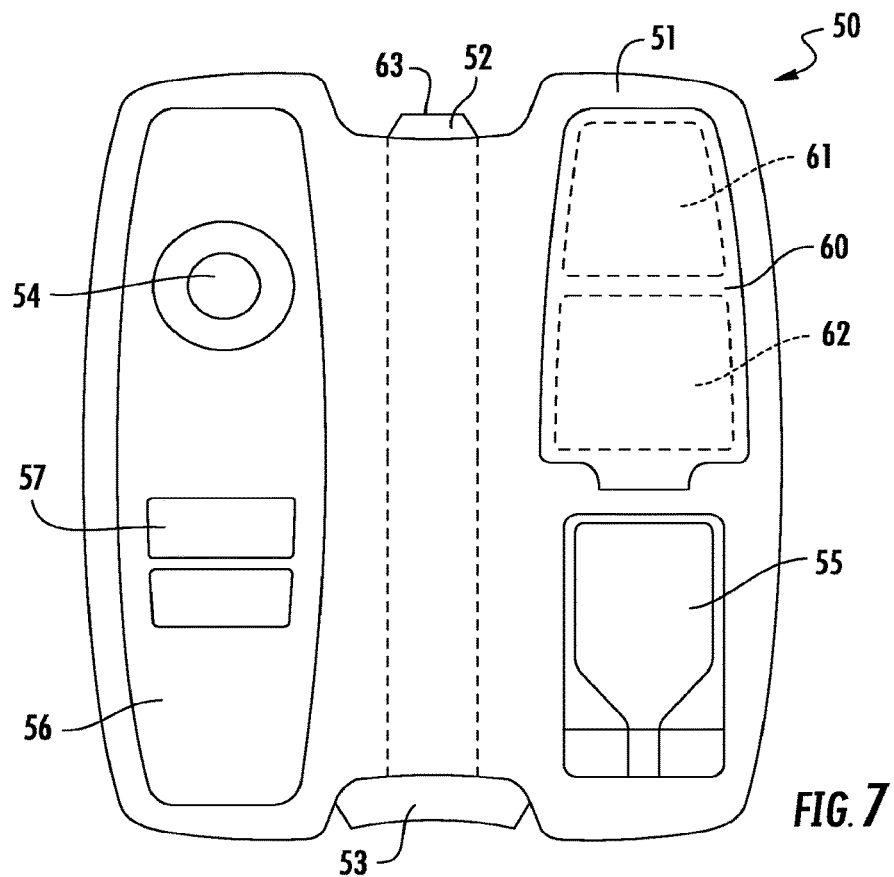
FIG. 7 shows a top view of the embodiment of FIG. 6.
Figure 8:
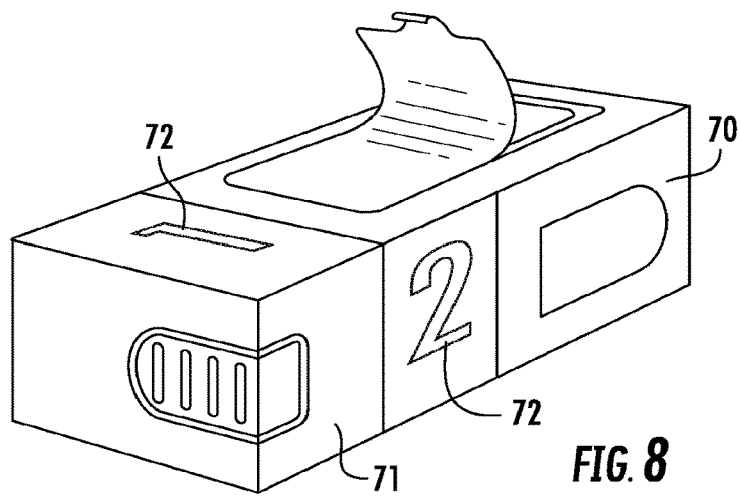
FIG. 8 shows an isometric view of a third embodiment of the present system.
Figure 9:
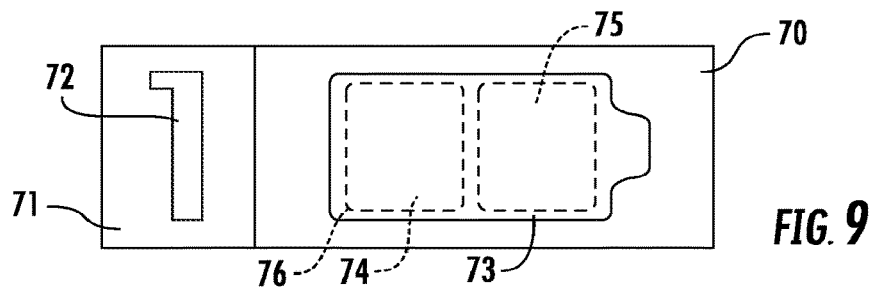
FIG. 9 shows a side view of the embodiment of FIG. 8.
Figure 10:
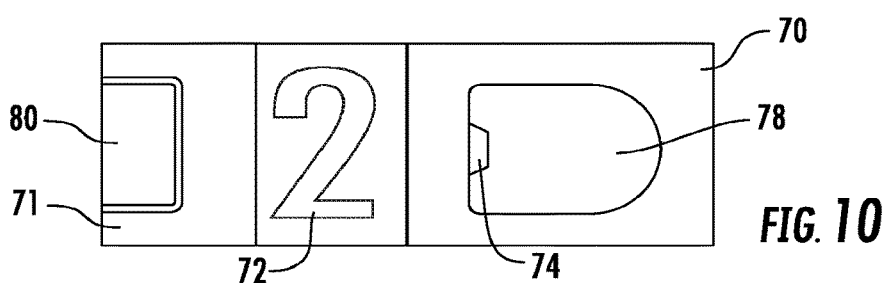
FIG. 10 shows a second side view of the embodiment of FIG. 8.
Figure 11:
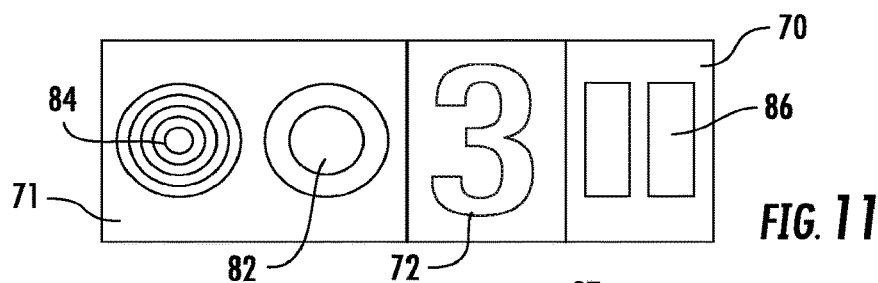
FIG. 11 shows a third side view of the embodiment of FIG. 8.
Figure 12:
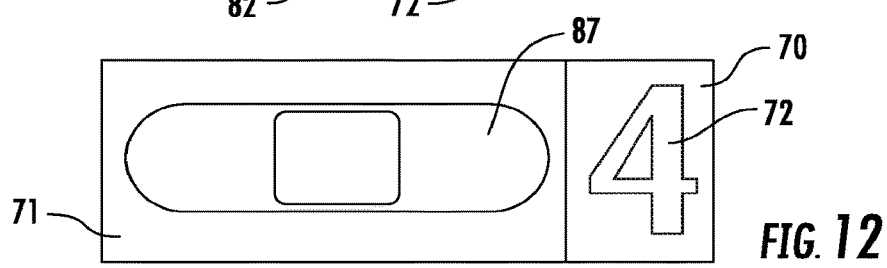
FIG. 12 shows a fourth side view of the embodiment of FIG. 8.

In a second embodiment of the present diagnostic system, shown in FIGS. 6 and 7, the diagnostic system (50) comprises a body (51) in the form of a substantially H-shaped housing.

In the illustrated form, the housing includes an integrated lancet (52) which extends substantially through the housing (51). The lancet (52) is moveable between a rest position in which the lancet tip is enclosed within the body (51) and an actuated position in which the lancet tip extends from the body (51). The lancet (52) is actuated by a lancet activator (53) positioned at one end of the body (51).

While the illustrated form includes a membrane penetration element in the form of a lancet, persons skilled in the art will be aware that the, membrane penetration element could be any piercing, slicing, cutting, puncturing or pricking element which allows a user to penetrate a membrane such as the skin to allow a fluid sample to be released.

The diagnostic system further comprises a blood collection window (54) in which a user places their pricked finger in order to collect blood expelled from the finger after the lancet pierces the finger. The blood collection window is positioned in line with a test material which is incorporated into the diagnostic system (50). A receptacle for buffer solution (55) is positioned on the diagnostic system (50). The receptacle (55) is in the form of a sachet of buffer solution which can be manually added to the blood in the blood collection window (54).

The lateral flow test strip (56) extends across one portion of the diagnostic system such that the blood collection window (54) and a results window (57) are both positioned above the lateral flow test strip (56). Buffer (55) is added to a blood collection window (54) and results appear in the results window (57).

In use, a user will peel foil (60) positioned over an alcohol swab and dry wipe (61 and 62). They will then clean their finger with the alcohol swab (61) and dry it with the dry wipes (62). The user will then place the pad of the finger against the integrated lancet (52) at point (63).

Lancet activation is brought about by contact with button (53). In the illustrated form, lancet activation comprises extension of the penetrating element of the lancet and retraction of the same into a housing to provide for safe storage and disposal. In the extended position, the penetrating element is adapted to lance, pierce, slice, prick or otherwise penetrate the users finger positioned at point (63). Blood is then collected at blood collection window (54). The receptacle of buffer (55) is then removed from the body and the solution is added to the blood collection window (54). The lateral flow test strip extends across the body (51) at lateral flow test strip (56) allowing results to be read in the results window (57).

In a third embodiment a diagnostic system (70) comprises a body (71) in the form of a housing having six sides. The sides are labelled with indicia (72) indicating the order of which the sides are to be used. A user will initially peel foil (73) from over an alcohol swab and dry wipe (74 and 75) which are positioned within an alcohol swab locator in the form of a depression (76) in one side of the diagnostic system (70). The user will clean their finger with the alcohol swab and then will insert their finger into finger pad depression (78) on a second side of the diagnostic system (70). An integrated lancet (79) is positioned within this side and actuated by lancet activator (80). Once the user has contacted lancet activator (80) the lancet tip extends from the body (71) to pierce a finger in the aperture (78). The lancet tip then retracts. The user then allows their blood to be collected at blood collection window (82) on a third side of the diagnostic system (70).

A solution delivery actuator (84) is positioned on the same side of the diagnostic system (70) as the blood collection window (82). Depression of the solution delivery actuator delivers a physiologically acceptable solution or buffer to the lateral flow test strip. The lateral flow test strip is incorporated into the diagnostic system (70) although it is not visible from' the outside of the system. The blood collected at blood collection window (82) and the buffer solution released upon depression of solution delivery actuator (84) combine to allow the test strip or other test material to provide results in the results window (86). The user then peels an adhesive strip from the adhesive bandage locator (87) located in the fourth side of the system. The adhesive bandage can then be used to bandage the pierced finger.

Figure 13:
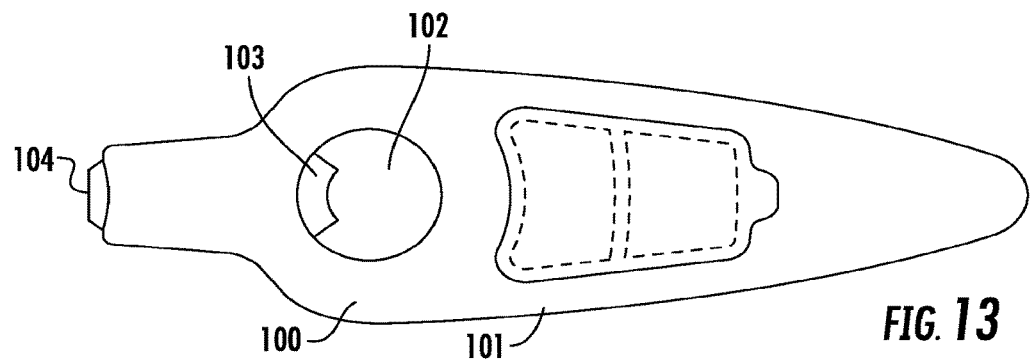
FIG. 13 shows a top view of a fourth embodiment of the present system.
Figure 14:
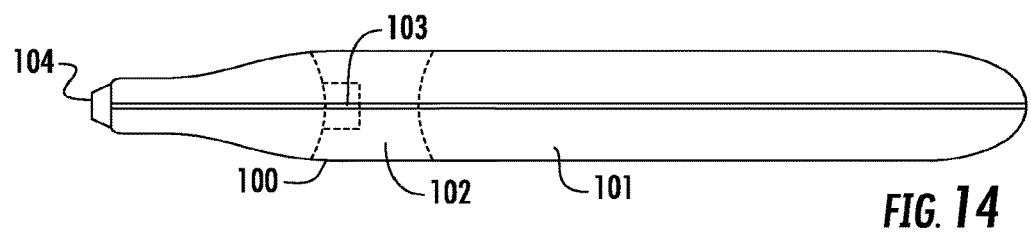
FIG. 14 shows a side view of the embodiment of FIG. 13.
Figure 15:
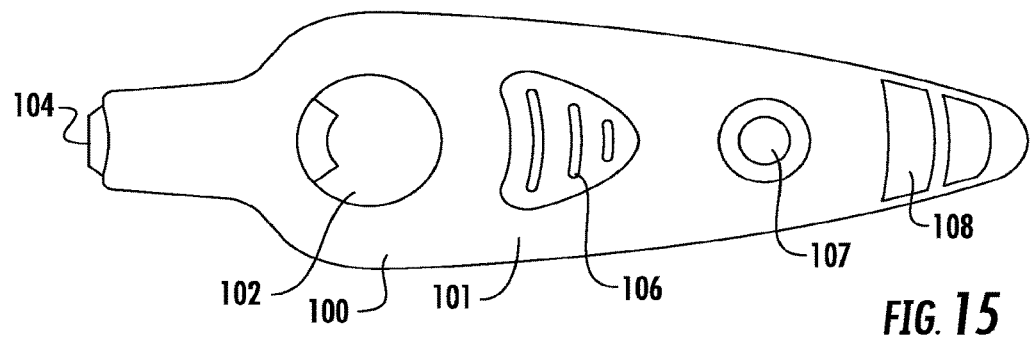
FIG. 15 shows a bottom view of the embodiment of FIG. 13.

A fourth embodiment is shown in FIGS. 13 to 15. In this embodiment a diagnostic system (100) comprises a body (101) in the form of an elongate housing. The body (101) includes a finger pad aperture (102) which is positioned adjacent a lancet (103). The lancet (103) is integrated into the body (101) and is moveable between a position in which the lancet tip is enclosed within the body (101) and a position in which the lancet tip extends from the body into the finger pad aperture (102).

The diagnostic system further comprises a lancet activator (104) which is actuated to move the lancet between the rest position in which it is enclosed in the body (101) and the actuator position in which it extends into the finger pad depression point (102). The reverse side of the body (101) comprises a solution delivery actuator in the form of a push button (106), along with a blood collection window (107) and results window (108).

In use, a user inserts their finger into the finger pad aperture (102) with the finger pad pressing against the integrated lancet (103). The user then actuates the lancet (103) by pressing lancet actuator (104). This acts to pierce the finger. The user then collects blood in blood collection window (107) and presses solution delivery actuator (106) to allow buffer solution or other physiologically acceptable solution to contact the blood in blood collection window (107) and the lateral flow test strip which is incorporated into the diagnostic system. The lateral flow test strip then provides a result at results window (108).

Figure 16:
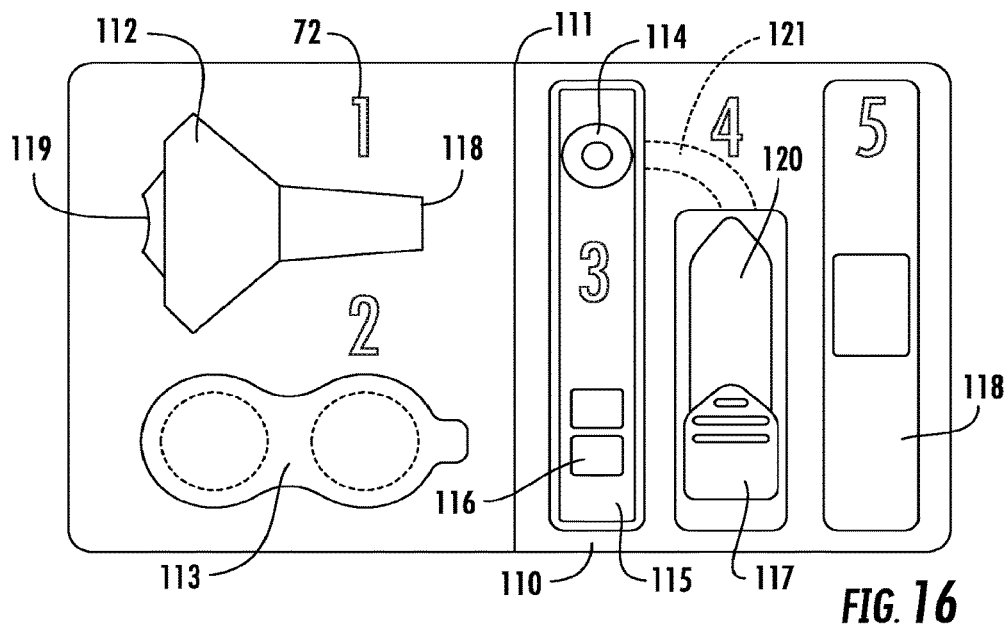
FIG. 16 shows a top view of a fifth embodiment of the present system.
Figure 17:
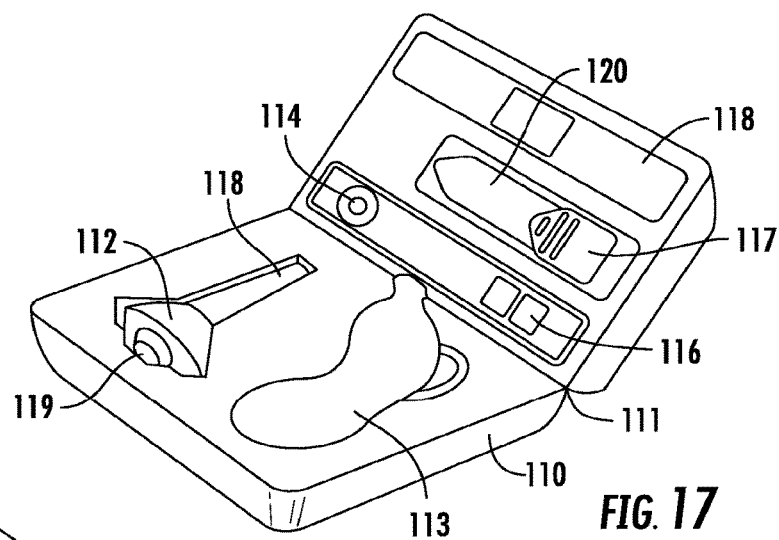
FIG. 17 shows an isometric view of the embodiment of FIG. 16.
Figure 18:
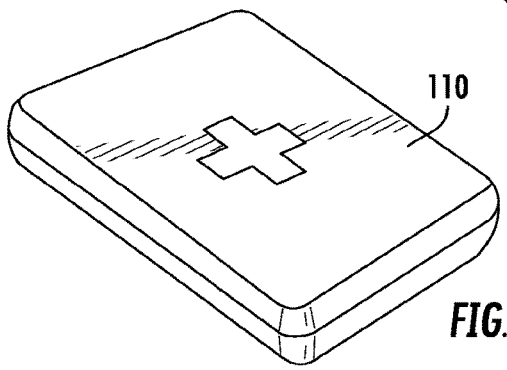
FIG. 18 shows an isometric view of the embodiment of FIG. 16 in a closed position.

A fifth embodiment of the present diagnostic system is shown in FIGS. 16 to 18. In this form the system is in kit form and the support member comprises a hard cover case (110). The hard cover case is hinged along a central hinge (111) and opens to reveal a removable lancing system (112), an alcohol swab, and dry wipe locator (113) a blood collection window, (114) a lateral flow test strip, (115) a results window, (116) a solution delivery actuator, (117) and an adhesive bandage locator (118).

In use, a user removes the foil from alcohol swab and dry wipe locator (113) to clean a finger for use. The user then removes the removable lancet (112) from the hard cover case (110) and positions their finger at the piercing end (118) of the integrated lancet (112). The user then depresses lancet actuator (119) to pierce the finger.

Blood is collected at blood collection window (114) above test strip (115). A buffer solution reservoir (120) is located in the body and is connected with the test strip (115) by a channel (121). The user slides solution delivery actuator (117) forward to direct the buffer to the test strip and results are provided in the results window (116).

In a sixth embodiment, shown in FIGS. 19 through 21, disclosed is a composite diagnostic system (140). The diagnostic system 140 may in one form be hand held.

Alternatively the system may be sized to be utilised as a table top system. The diagnostic system (140) comprises a support member (142) which is made up of a body (143) in the form of a housing having an elongated oval shape. The body (143) comprises top face (144) bottom face (145) and sides (146) and extends from a distal end (147) at which the lancet is positioned to a proximal end (148).

The diagnostic system further comprises an integrated lancet (149). The integrated lancet is positioned in the distal end (147) of the body (143) and is surrounded by the external walls of the body. A lancet tip (151) is positioned in a rest position internally to the body (142). The lancet tip (151) is positioned to extend from the body (142) when the lancet is actuated. In the actuated position, the lancet tip (151) extends from the body such that a finger positioned at the distal end is pierced by the lancet upon the lancet moving between the rest position and the actuated position. The lancet tip (151) then retracts into the body (143).

In use, activation of the lancet between the rest position and the actuated position occurs through depression of a lancet activator (153) which extends from the distal end (147). A user places their finger against a protruding end (155) of the lancet (149) and this contact results in depression of the lancet activator (153) moving the lancet tip (151) to pierce a finger or alternative body part positioned at the distal end (147).

Upon a users finger being pierced by the lancet, the user or clinician moves the user's finger over the fluid collection element (156) which, in the illustrated form, is in the form of a window. Bodily fluid, in this case blood, is collected at fluid collection element (156). The fluid collection element (156) is positioned proximal to the distal end (147) to allow a user to easily move the pierced finger to the fluid collection element (156) without depositing fluid other than in the element.

While the fluid collection element (156) has been described in the form of a window into which fluid is deposited, the collection element (156) could alternatively be in the form of a capillary tube which may be adapted to retain and deposit quantifiable amounts of fluid, an alternate opening or depression, a loop adapted to retain and deposit small amounts of fluid, a well or any alternative embodiment which allows for deposit of fluid and transfer or movement or placement onto the test material within the system.

The diagnostic system further comprises a physiologically acceptable solution such as a buffer stored in a buffer sachet (159) for supporting the blood or other bodily fluid. A solution delivery actuator (160) is positioned on the diagnostic system. Contact with the solution delivery actuator (160) releases the buffer solution from the sachet (159).

A test material in the form of a test strip (162) is positioned beneath the buffer sachet (159) and the fluid collection window (156). The test material in the illustrated form comprises a lateral flow test strip, however it may comprise a vertical flow test strip, solid phase test material, agglutination test material, a cartridge or reagent tube or any element which incorporates a reagent adapted to be mixed with the bodily fluid, a card incorporating a fluid sample retention material, an assay, a test strip or an integrated electrical circuit.

The diagnostic system further includes a results window (164) which is positioned on the same side as the fluid collection window (156) for easy viewing of the results of any diagnostic test performed.

An alcohol swab locator (165) in the form of indicia or a depression or other location feature in which alcohol swabs and dry wipes can be inserted or attached is positioned in a surface of the support member such as in the illustrated form in side (146).

An adhesive bandage locator (167) is positioned in the proximal end (148) of the diagnostic system (140). The adhesive bandage locator is in a form of a slit extending into the body (142) of the system (140) which fits adhesive bandages such as Band-Aids™.

In a seventh embodiment shown in FIGS. 22 through 26 disclosed is a composite diagnostic system (140). The diagnostic system (140) comprises a support member (142) which is made up of a body (143) in the form of a housing having an elongated oval shape. The body (143) comprises top face (144) bottom face (145) and sides (146) and extends from a distal end (147) at which a lancet is located to a proximal end (148).

The diagnostic system further comprises an integrated lancet (149). The integrated lancet is positioned in the distal end (147) of the body (143) and is surrounded by the external walls of the body. A lancet tip (not illustrated in this form) is positioned in a rest position internally to the body (142). The lancet tip is positioned to extend from the body (142) when the lancet is actuated. In the actuated position, the lancet tip extends from the body such that a finger positioned at the distal end is pierced by the lancet upon the lancet moving between the rest position and the actuated position. The lancet tip thereafter retracts into the body (143) to allow for safe storage or disposal of the system.

In use, activation of the lancet between the rest position and the actuated position occurs through depression of a lancet activator (153) which extends from the distal end (147). A user places their finger against a protruding end (155) of the lancet (149) and this contact results in depression of the lancet activator (153) moving the lancet tip to pierce a finger or alternative body part positioned at the distal end (147).

Upon a users finger being pierced by the lancet, the user or clinician moves the user's finger over the fluid collection element (156) which, in the illustrated form, is in the form of a window. Bodily fluid, in this case blood, is collected at fluid collection element (156). The fluid collection element (156) is positioned proximal to the distal end (147) to allow a user to easily move the pierced finger to the fluid collection element (156) without depositing fluid other than in the element. While the fluid collection element (156) has been described in the form of a window into which fluid is deposited, the collection element (156) could alternatively be in the form of a capillary tube which may be adapted to retain and deposit quantifiable amounts of fluid, an alternate opening or depression, a loop adapted to retain and deposit small amounts of fluid, a well or any alternative embodiment which allows for deposit of fluid and transfer or movement or placement onto a test material.

The diagnostic system further comprises a physiologically acceptable solution such as a buffer stored in a buffer sachet (159) for supporting the blood or other bodily fluid. A solution delivery actuator (160) in the form of a slide is positioned on the diagnostic system. Sliding the solution delivery actuator (160) into an actuated position (shown in FIGS. 25 and 26) releases the buffer solution from the sachet (159).

A test material in the form of a test strip (162) is positioned beneath the buffer sachet (159) and the fluid collection window (156). The test material in the illustrated form comprises a lateral flow test strip however it may alternatively comprise a vertical flow test strip, solid phase test material, agglutination test material, a cartridge or reagent tube or any element which incorporates a reagent adapted to be mixed with the bodily fluid, a card incorporating a fluid sample retention material, an assay, a test strip or an integrated electrical circuit.

In one form the test material is adapted to interface with diagnostic equipment to provide a diagnosis. In one form the test material is removably engaged with the diagnostic system and is adapted upon removal to interface with diagnostic equipment for diagnosis. For example, a test strip may be removable and able to be inserted into diagnostic equipment for analysis. In another form a portion of the system such as a cartridge containing the test material or a fluid retainer is removable from the system to interface with diagnostic equipment.

Alternatively the system may include a port or platform for engagement with diagnostic equipment. The port may be in the form of a window or opening in contact with the test material. The diagnostic system can then interface with diagnostic equipment to be analysed and provide a diagnosis.

The diagnostic system further includes a results window (164) which is positioned on the same side as the fluid collection window (156) for easy viewing of the results of any diagnostic test performed. The results window (164) in this embodiment is positioned under the solution delivery actuator (160) when it is in a rest position (shown in FIGS. 22 and 23) and is revealed when the solution delivery actuator (160) is in an actuated position (shown in FIGS. 25 and 26). In the actuated position the fluid collection window (156) is covered by the solution delivery actuator (160).

An alcohol swab locator (165) in the form of a depression in which alcohol swabs and dry wipes can be inserted is positioned on the top face (144).

An adhesive bandage locator (167) is positioned in the distal end (148) of the diagnostic system (140). The adhesive bandage locator is in a form of a slit extending into the body (142) of the system (140) which fits adhesive bandages such as Band-Aids™.

Figure 27:
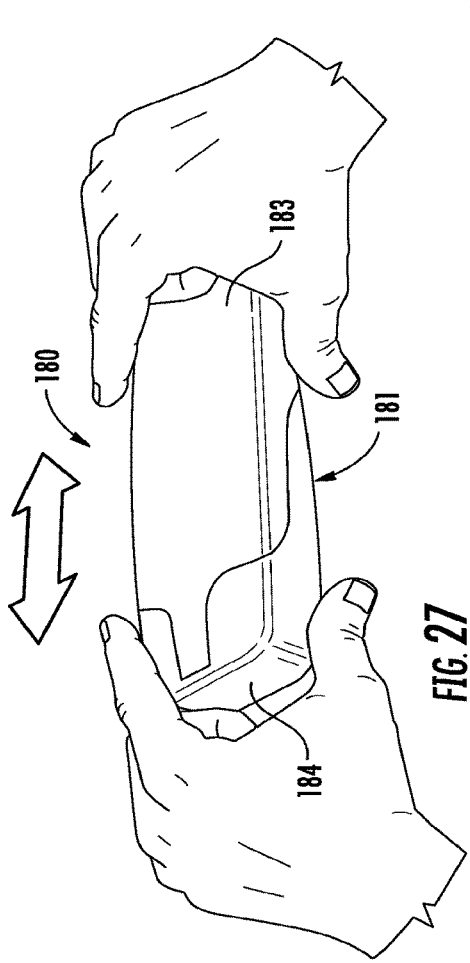
FIG. 27 shows a perspective view of an eighth embodiment of the present system in a closed position.
Figure 28:
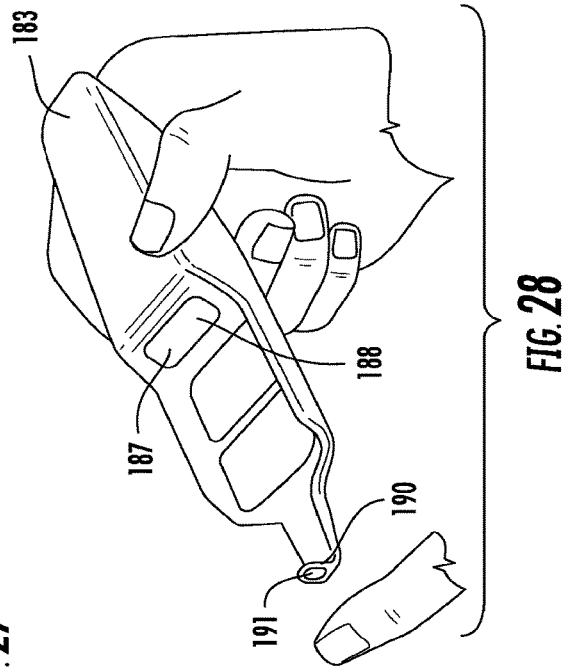
FIG. 28 shows a perspective view of the embodiment of FIG. 27 in use.
Figure 29:
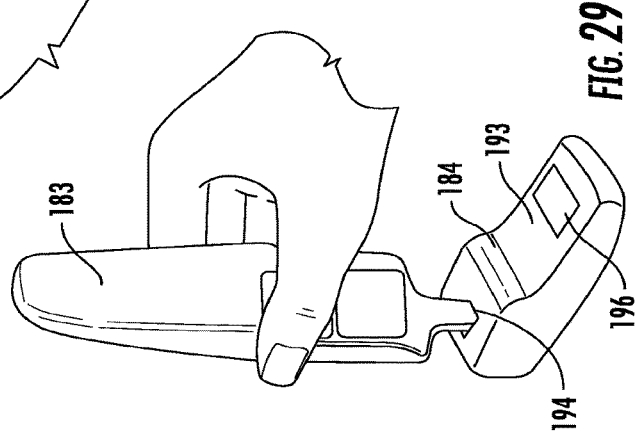
FIG. 29 shows a perspective view of the embodiment of FIG. 27 in use.

FIGS. 27 through 29 show an eighth embodiment of a diagnostic system. The diagnostic system (180) comprises a body (181) composed of a sampling section (183) and a diagnostic section (184). The sampling section (183) and the diagnostic section (184) are removably engaged with one another. In the illustrated form the diagnostic section (184) caps the sampling section (183) and is engaged by means of a connector, clip, interference fit, snap fit or other engagement method.

The sampling section (183) comprises a sampling body (186). The sampling body (186) is adapted to be held in one hand, although the body (186) could alternatively be rested on a surface. A membrane penetration element (not illustrated in this form) in the form of a lancet is largely enclosed in the body (186). A lancet tip (not illustrated) is positioned to extend from the body (186) through a lancet opening (187) in an actuated position and retract back into the body thereafter. Actuation of the lancet occurs through pressure on a lancet actuation element (188).

In the illustrated form the membrane penetration element has been described in terms of a lancet, however any other piercing, pricking, slicing, or otherwise penetrating element may be utilised. Of course, the present invention may be applied in contexts where no such piercing element is required, for example urine testing.

The sampling section (183) further includes a fluid collection element (190). In the illustrated form the fluid collection element (190) is in the form of a loop (191) although the fluid collection element may comprise a well, window, capillary tube or any alternative element for fluid collection.

A user positions a body part such as a finger adjacent the lancet opening (187) and actuates the lancet through pressure on the lancet actuation element (188). The lancet penetrates a membrane on the body part releasing a fluid, in this case blood. The user positions the body part in contact with the loop (191) and deposits a sample of blood therein.

The diagnostic section (184) comprises a body (193) which in this form is placed on a surface. The body includes a fluid deposit opening (194) into which the fluid collection element (190) on the sampling section (183) can be inserted to deposit fluid from the loop (191). A test material (not illustrated) is positioned within the body (193) such that fluid from the sampling section (183) interacts with the test material. In the illustrated form the test material is in the form of an integrated lateral flow test strip, test strip, cassette, cartridge, integrated circuit or other diagnostic or pre-diagnostic element.

The diagnostic section (184) further includes a test result window (196) through which results of a diagnostic test can be displayed. The illustrated form shows an integrated test material resulting in an on-site diagnosis, however a person skilled in the art will be aware that the test material could be adapted to be analyzed elsewhere and a diagnosis provided by separate diagnostic equipment.

As shown best in the first and third embodiments, indicia (72) are incorporated onto the system to visibly cue a user to perform a sequence of steps in order. In the illustrated embodiment the indicia are in the form of numbers, however it will be clear that graphic, pictorial, text or alternative indicia could effectively present the sequence of steps to cue a user. In the first embodiment, the indicia (72) instruct the user to first perform the step on the side labelled "1", that is, clean and dry the area of skin in preparation for lancing. The user then rotates the system to find step "2", in which the user inserts a finger into the finger pad aperture (29) for lancing. The user then activates the lancet (28). The user rotates the system to find step "3" in which the user deposits blood at the blood collection window (32). The physiologically acceptable solution and blood contact the test material and the results show in the results window on the front face. The user then rotates the system to perform step 4, placing an adhesive bandage on the finger.

In the third embodiment the steps are much the same, however the step of delivering physiologically acceptable solution to the test material is performed by actuating an actuator (84) positioned adjacent the blood collection window (82). In one not illustrated form, a detachable patient information card or label is affixed to the support member.

In one not illustrated form, the diagnostic system is modular, comprising a body incorporating the membrane penetration element and a cartridge, the cartridge incorporating the fluid collection element and test material and, in some forms, a physiologically acceptable solution such as a buffer and a test results window. In this form, manufacture comprises separately manufacturing the body incorporating, for example, a lancet and the cartridge. Separate manufacture allows selection of specific cartridges for use in a given order.

It will be appreciated that while the embodiments described envisage an integrated lancet, the present invention could be implemented using a separate lancet device or other membrane penetration device, or using a fluid which is directly sampled of discharged from another device (e.g. a syringe). For example, in a point of care situation, it may be more convenient for staff to use conventional disposable lancets with a test unit according to the present invention.

Similarly, the term buffer is used broadly, and is intended to cover both fluids that are strictly buffer fluids, as well as any fluid required to be dispensed before or after the sample is applied to the test component. The fluid may be any kind of fluid which is used to facilitate, activate, optimise or otherwise be sued with the test. It may be a, in some cases, a simple aqueous solution to reduce the viscosity of a blood sample to assist with chromatography. It may be a simple diluent or running buffer, or a more complex fluid with specific components o properties to make the test component perform better, or at all. The present invention is applicable to any type of fluid that is required to be added before, during or after the test sample is applied.

Figure 30:
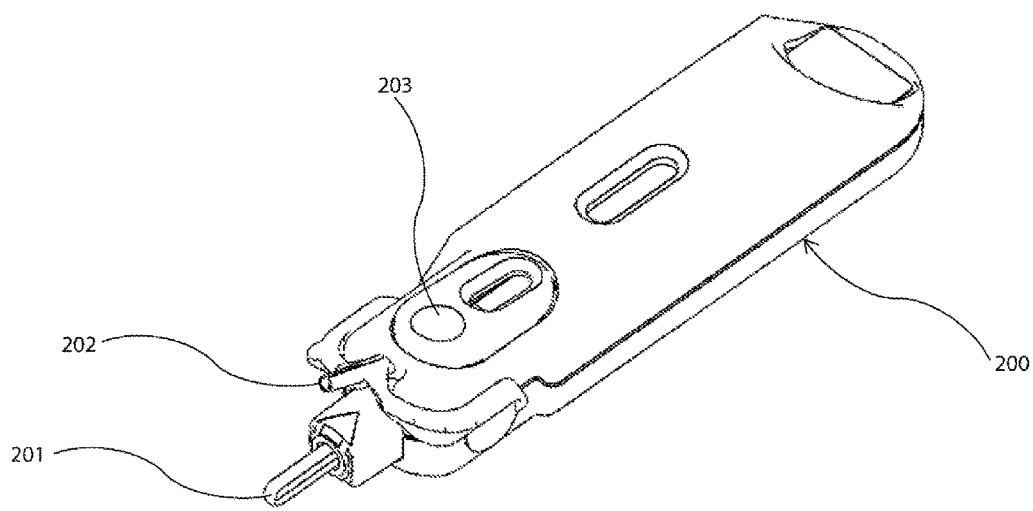
FIG. 30 shows a perspective view of a ninth embodiment.

FIGS. 30 to 34 illustrate a further embodiment of the present invention. FIG. 30 show the test unit 200 including a button 203 for release of buffer, a fluid collection tube 202, and a lancet component 201.

Figure 31:
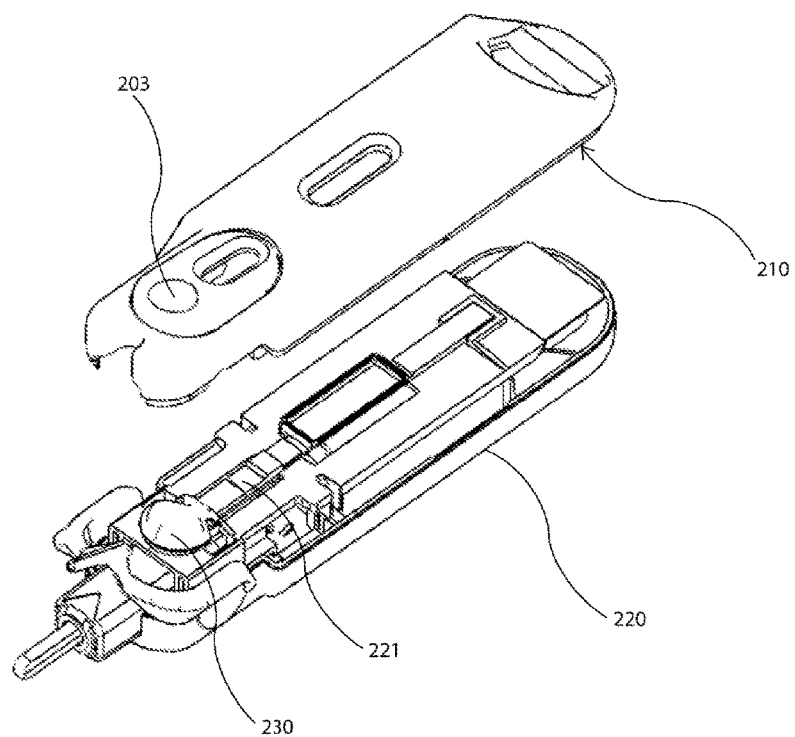
FIG. 31 shows as partly disassembled view of the embodiment of FIG. 30.
Figure 32:
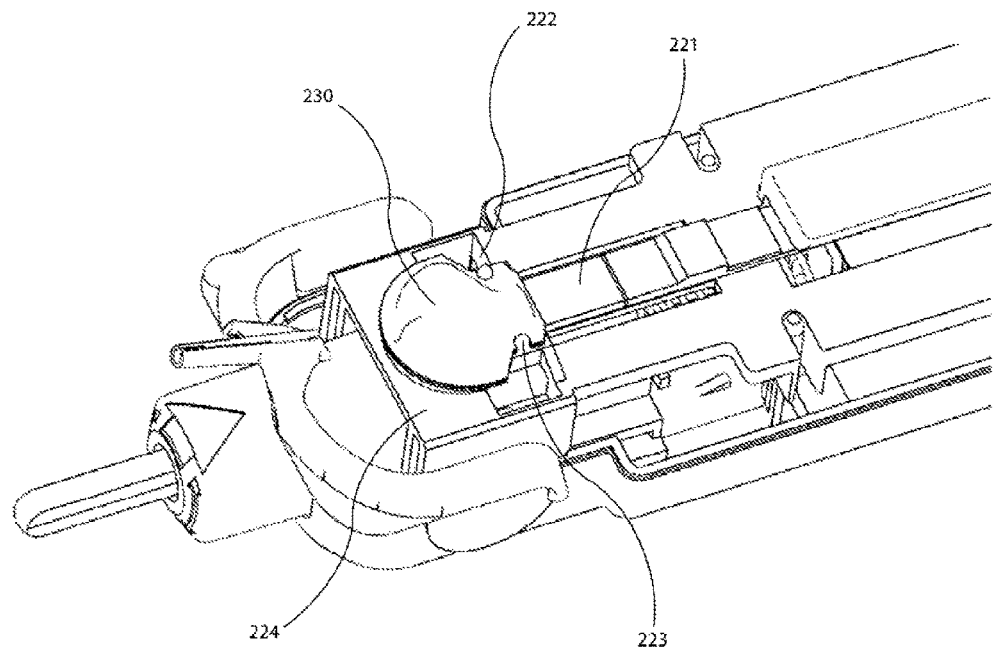
FIG. 32 shows a detailed view of part of FIG. 31.

FIG. 31 illustrates the unit in a partly disassembled form. The top housing 210 includes the push button 203. In the lower housing 220, beneath the button 203 in the assembled state, is a sachet 230 of a buffer solution. It will be appreciated that this fluid could be any suitable fluid required to assist the test process, and the term buffer is used for convenience only.

Buffer sachet 330 sits on the lower housing 220 adjacent to the test strip 221. As can be better seen in FIG. 32, buffer sachet 230 rests on a platform 224, which includes location bosses 222, 223. These serve to assist in locating buffer sachet 230 in the correct position during manufacture.

Figure 33:
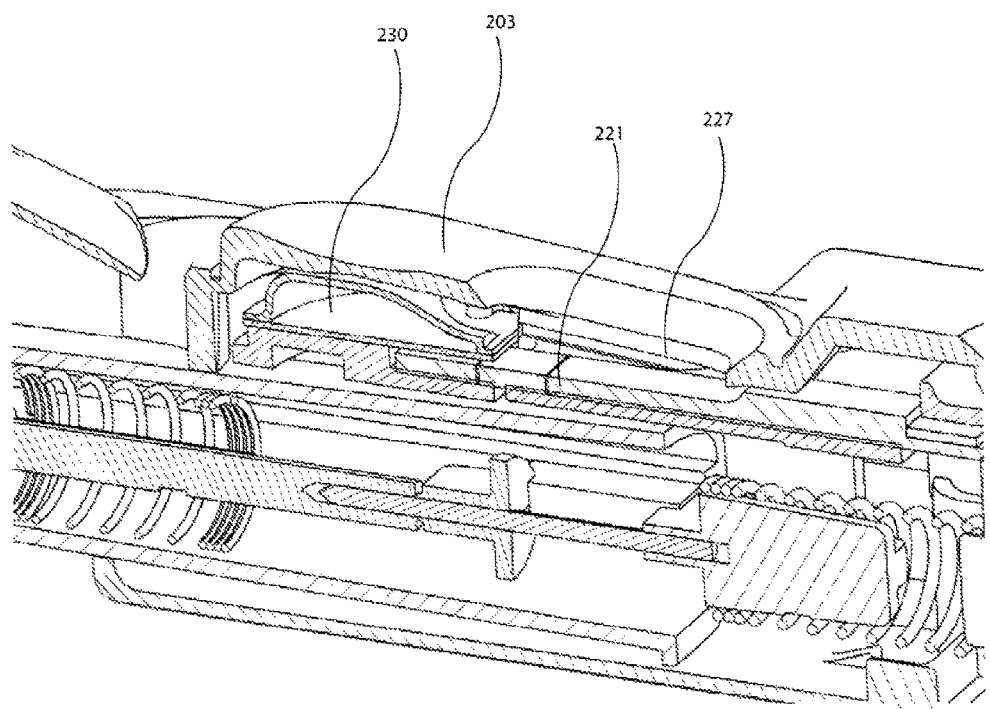
FIG. 33 shows a perspective view in section of the embodiment of FIG. 30 in a ready position.

FIG. 33 illustrates the assembled test unit, and in particular the portion associated with buffer sachet 230 and test strip 221. Buffer sachet 230 can be seen in position underneath button 203.

Figure 34:
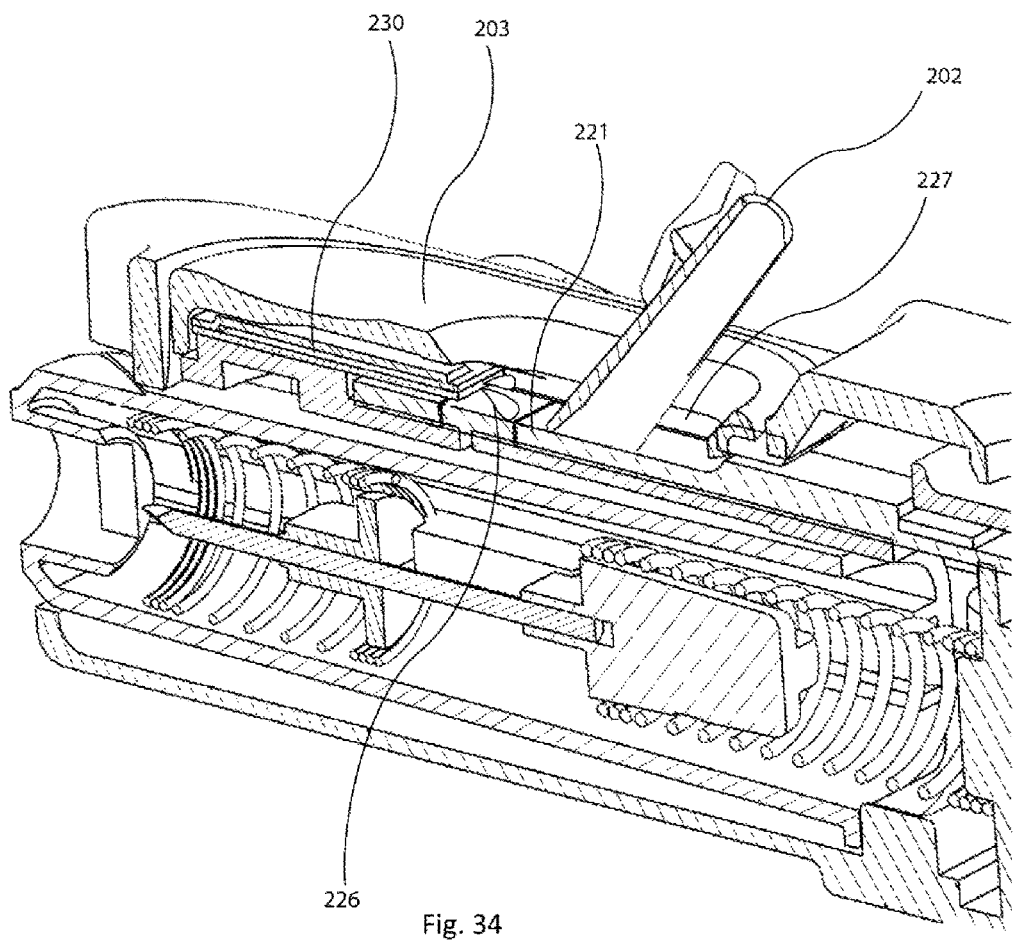
FIG. 34 shows a perspective view in section of the embodiment of FIG. 30 in a buffer release position.

In FIG. 34, fluid collection tube 202 has been moved into the discharge position, so that the collected fluid is discharged onto the test strip. As the buffer solution is now required, button 203 is depressed. Buffer sachet 230 is compressed and the fluid forced out, to release point 226. The buffer solution (not shown) is contained by the side walls 227, so that it is taken up by the test strip.

It will be appreciated that a particular advantage of this arrangement is that a carefully controlled volume of buffer is provided to the test strip, allowing for accurate, error free application relative to prior art techniques.

Sachet 230 may be formed from any suitable impervious material, formed (for example by heat or RF welding) into a filled fluid enclosure, but designed to rupture under the correct level of force.

Figure 35:
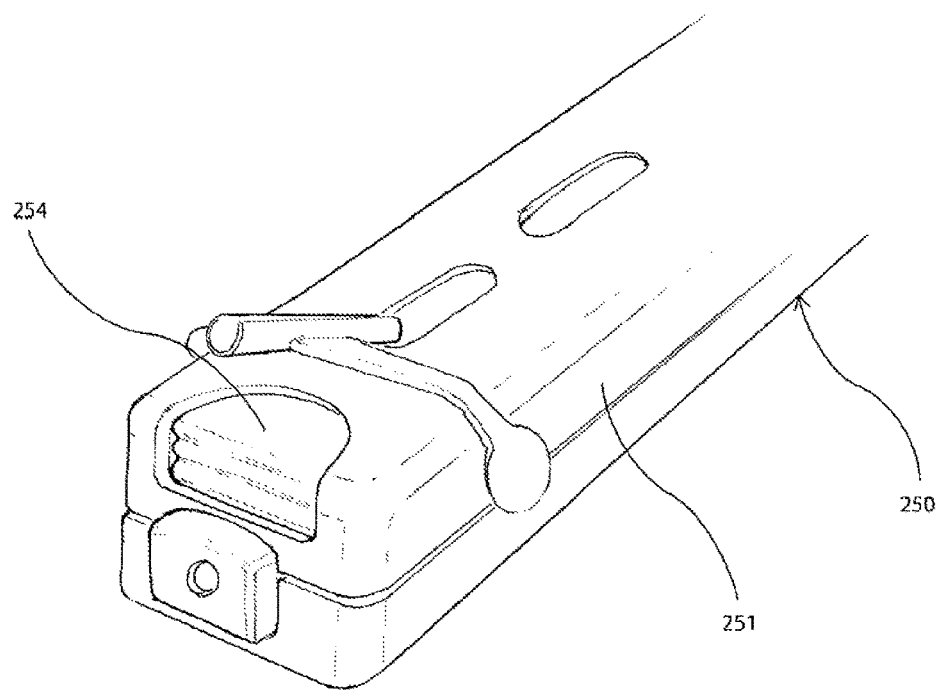
FIG. 35 shows a perspective view of a tenth embodiment.
Figure 36:
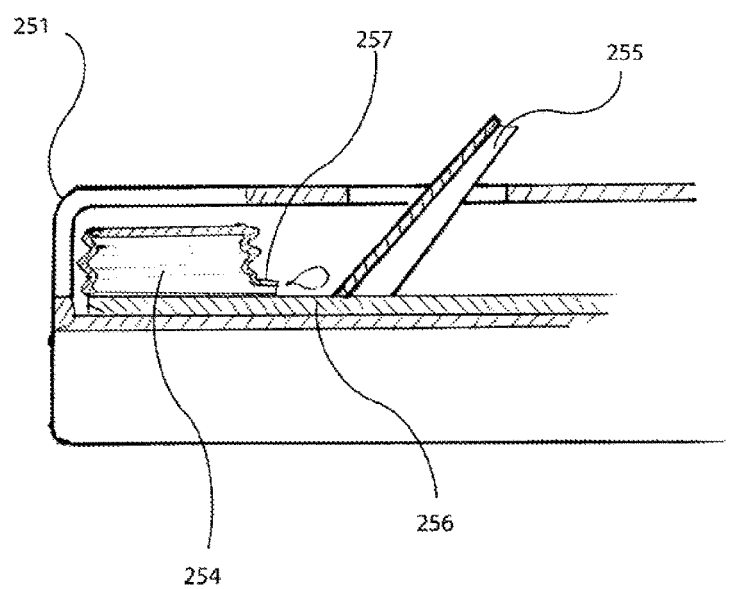
FIG. 36 shows a view in section of the embodiment of FIG. 35.

FIGS. 35 and 36 illustrate another implementation, particularly in relation to the construction of the buffer reservoir. In this arrangement, the buffer is in a concertina type reservoir, formed for example by blow moulding. Buffer reservoir 254 is located under the upper housing 254 of the test unit 250. The top of the buffer reservoir 254 is exposed, and can be depressed, as illustrated by the arrow in FIG. 36. This releases buffer fluid through a directed opening 257 onto the test strip 256. Again, the fluid collection tube 255 has been moved into the discharge position and the fluid released prior to the buffer being discharged.

It will be appreciated that although the examples provided have been in the more usual situation where the buffer or other fluid is applied after the sample is placed onto the test strip, this is not a specific mechanical limitation of the device. The buffer could be applied, if appropriate to the test, before the sample is discharged. Alternatively, if the fluid was required to be applied in advance to the strip, for example in order to activate it, this can be readily accomplished using the fluid reservoir of the present invention. The potential for accurate, controlled dispensing which is provided by the implementations of the present invention may provide such additional options for designing and undertaking tests.

Figure 37:
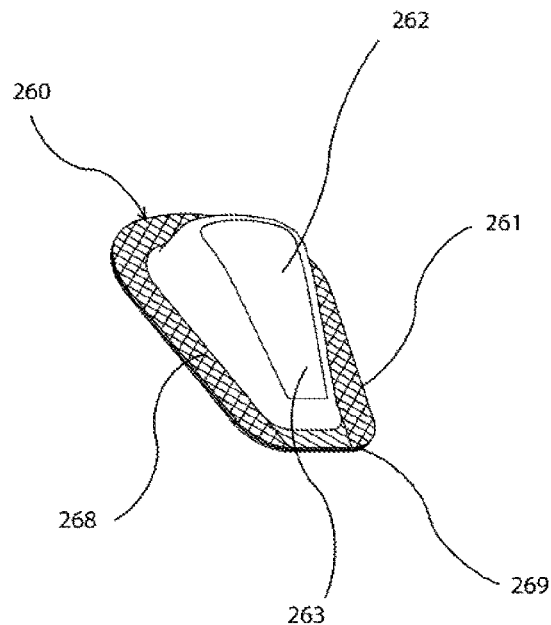
FIG. 37 shows a perspective view of a sachet for use with an eleventh embodiment.
Figure 38:
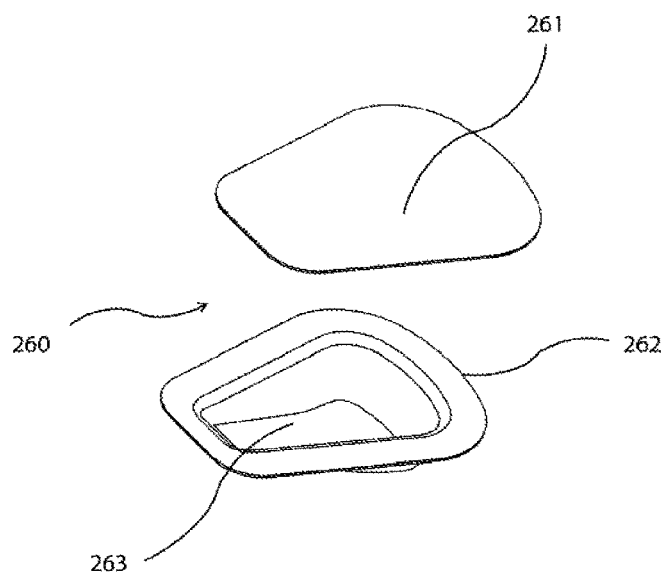
FIG. 38 is a view illustrating assembly of the sachet of FIG. 37.

FIGS. 37 and 38 illustrate another implementation of the buffer sachet. In this example, sachet 260 includes a housing 262 and a lower membrane 261. It can be seen that the reservoir 263 so formed tapers towards end 269. The seal between the housing 262 and lower membrane 261 provides a peripheral flange 268 around sachet 260.

The housing may be formed from any suitable material, having regard to the operational requirement to bond or seal, retain the selected buffer fluid, to need to provide stability, and reliability at the point when buffer discharge is required. A suitable material for housing 262 and membrane 261 may be a polymer such as PET, or a multilayer aluminium and polymer material.

The precise dimensions of the sachet will be determined in part by the volume of fluid required to be dispensed. For a dispensed volume of fluid of 80 µm, the sachet of the general shape shown in FIG. 37 may have an overall length of about 13 mm, a width of about 10 mm, with the housing having a width of about 3 mm at end 269. It will be appreciated that in any practical system, some of the fluid will be retained in the sachet even after release, and so allowance (e.g. as overfill) for this must be made in the filled volume. The seal is preferably a double seal around the periphery, apart from a small section, illustratively at end 269, which is single sealed, so that the fluid will preferentially discharge at that end when pressure is applied to the sachet.

FIG. 38 illustrates one approach to forming sachet 230 as shown in FIG. 37. The housing 262 is shown inverted relative to FIG. 37. Reservoir 263 is filled with the buffer solution. Lower membrane 261 is then placed into position and heat sealed to housing 262. It will be appreciate that the general approach to forming and filling such sachets is a well practiced art in medical, food preparation and related fields, and that such sachets can be readily manufactured in this way in considerable volumes.

Figure 39:
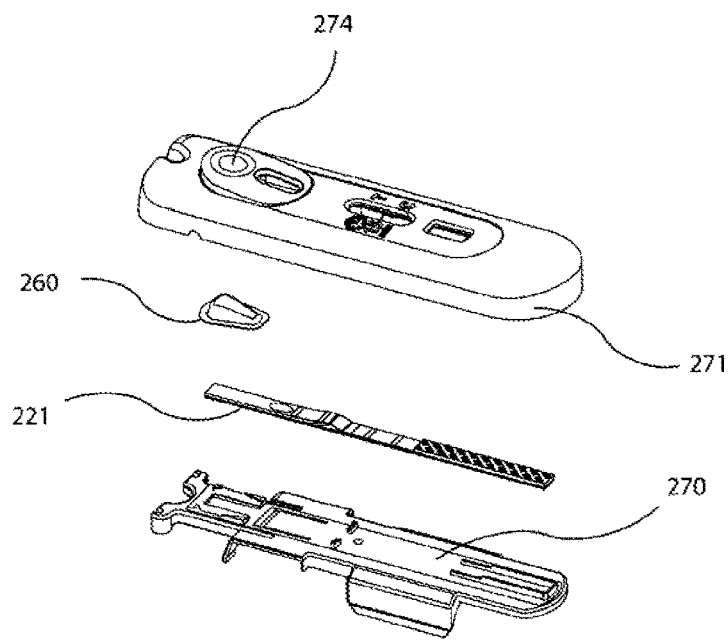
FIG. 39 is an exploded view of the eleventh embodiment illustrating assembly of the sachet into the housing.
Figure 40:
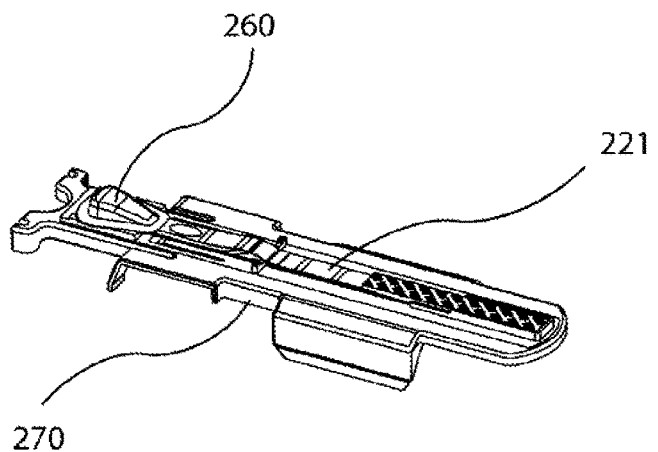
FIG. 40 shows a perspective view of the buffer sachet assembly of FIG. 39.

FIG. 39 illustrates the assembly of the illustrative sachet into a test unit. The test unit includes a test strip plate 270. Test strip 221 is located correctly into test strip plate 270. Buffer sachet 260 is then located into test strip plate 270, in this implementation partly overlying test strip 221. Finally, the top housing 271, which includes the button 274 which operative depresses buffer sachet 260, is located over the completed test strip plate assembly. The assembled components can be seen in FIG. 40.

Figure 41:
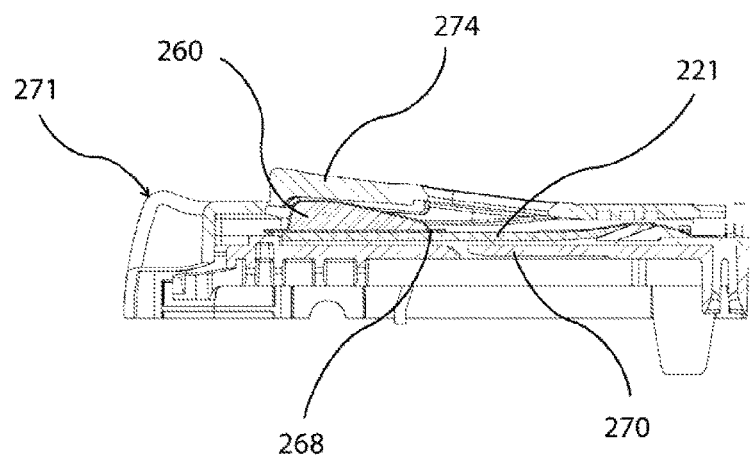
FIG. 41 shows a cross sectional view of the embodiment of FIG. 40.

FIG. 41 illustrates, partly in section, the operation of buffer sachet 260 and the associated mechanism in this implementation. A compressive force is first applied to button 274, which may be illustratively 5N. It will be appreciated that the required force is largely a consequence of the construction of buffer sachet 260. A balance between ease of use, by not requiring an excessive force, and accuracy and reliability in storage and preparation, which require the force for release to not be too small, is required.

The button compresses buffer sachet 260. Once the internal pressure is sufficiently high, the single seal region of sachet 260, adjacent to end 269, ruptures. This releases the contained buffer at the release point 268, onto the test strip 221.

It will be understood that there are many possible alternatives implementations to achieve the desired controlled release of the buffer fluid. For example, instead of a weakened seal region, the mechanism could employ a blade or sharpened projection to pierce the buffer sachet. The sachet may have a frangible or weakened portion which is not the seal. The sachet may include a valve, which releases fluid under sufficient pressure. The mechanism for compressing the buffer sachet, instead of being of lever or button type, could operate by sliding or rotation. Suitable channel or tube means could be used to guide the release buffer fluid to the intended location. The compression mechanism could be associated with another component of the integrated test unit, for example be engaged by a specific movement or release of the a fluid collection component.

In one implementation, shown in FIGS. 42 to 45, an interlock is provided to further assist the user in correct operation of the test unit. The principle is that until the lancet has been activated, the blood collection unit cannot be moved into the delivery position, and that until the blood collection unit has been moved into the delivery position, the buffer cannot be released. It will be understood that if, for example, it was required that a test fluid be dispensed to the test component before the sample was delivered to the test component, comparable interlock mechanisms could be used.

Figure 42:
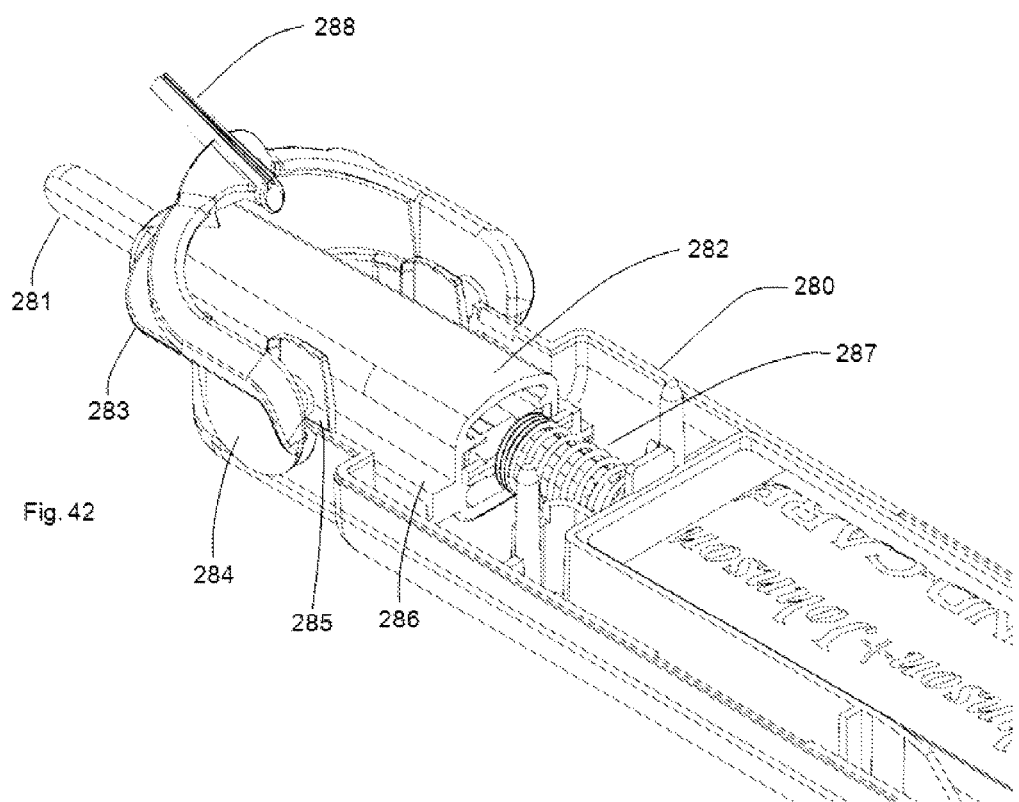
FIG. 42 is a perspective view, partly cut away, illustrating a twelfth embodiment.
Figure 43:
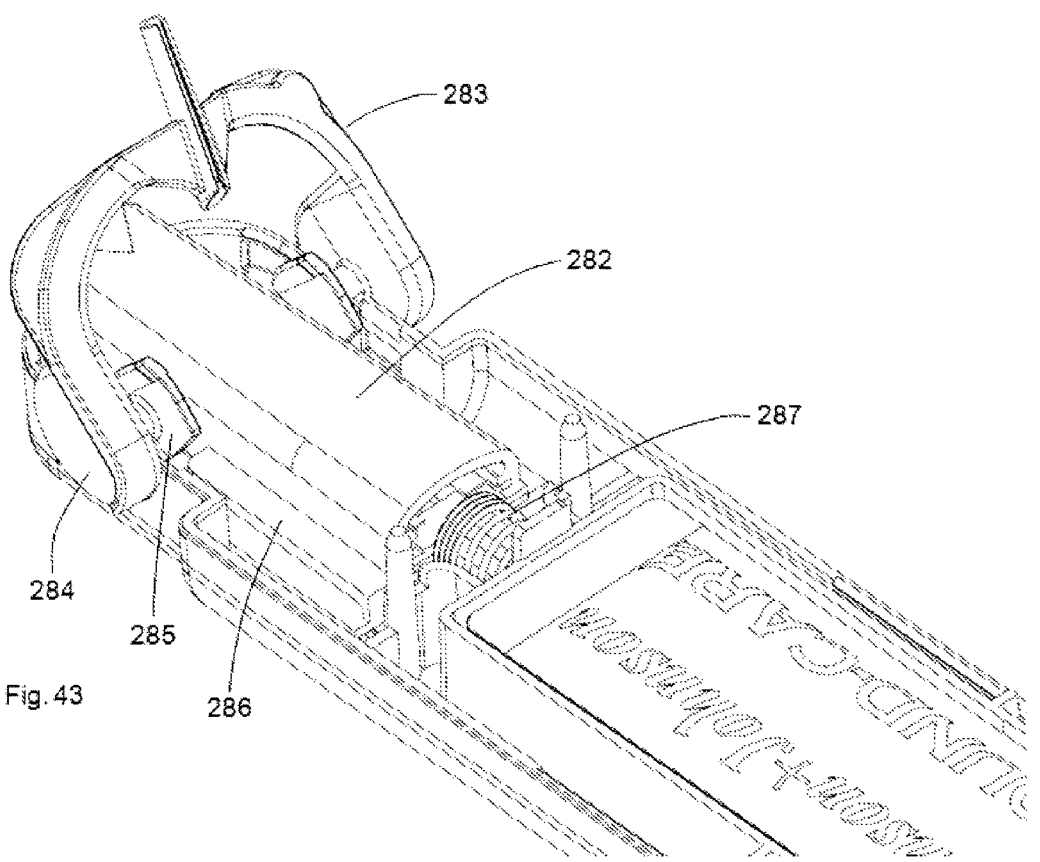
FIG. 43 is view similar to FIG. 42 but in a second position.

FIG. 42 illustrates one end of test unit 280. In FIGS. 42 and 43, the top housing is not shown, to better facilitate understanding. It will be understood that this drawing is intended to particularly illustrate one implementation of an interlock. This approach may be applied to other suitable implementations described above. Moreover, the interlock may be applied only in part, for example to ensure buffer release after sample delivery in an implementation without an integral lancet device.

FIG. 42 shows the lancet assembly 281, with a sleeve 282 extending to spring 287. A shelf 286 extends along the side of sleeve 282. Blood collection arm 283 carries a capillary 288 for collecting a sample of blood. Blood collection arm 283 is rotatable about an axis, generally indicated as 284, in order to deliver the blood in capillary 288 to a test strip (not shown in this view).

However, in the state shown in FIG. 42, shelf 286 engages projection 285, thereby preventing rotation of the blood collection arm 283. Thus, rotation is prevented until the lancet has been operated.

FIG. 43 is a similar view to FIG. 42, but the lancet has been operated. The sleeve 282 has now moved longitudinally and compressed spring 287. Shelf 286 is accordingly moved forward, so that it no longer engages projection 285. Thus, blood collection arm 283 is able to rotate.

The same projection 285 is important in preventing release of the test fluid in this implementation, until the blood collection arm is rotated to the delivery position. This can be seen in FIG. 44. The top housing 290 can now be seen, including button 292. The recess 291 for delivery of the sample, and a part of the test strip 295 can also be seen.

Figure 44:
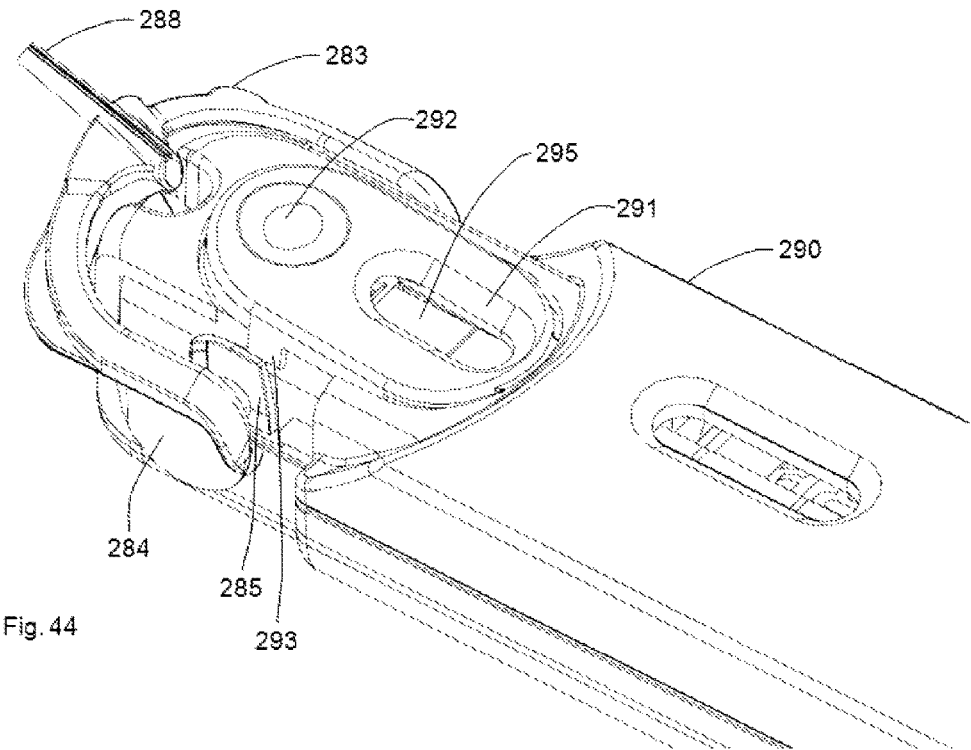
FIG. 44 shows a perspective view similar to FIG. 42, but not cut away.

In the position of FIG. 44, projection 285 on blood collection arm 283 engages foot 293 which extends from the top housing. Whilst foot 293 is engaged, the button 292 cannot be depressed, and hence the buffer sachet (not shown) cannot be depressed and the fluid released. Buffer release in this example is closely related to the mechanism in FIG. 41.

Figure 45:
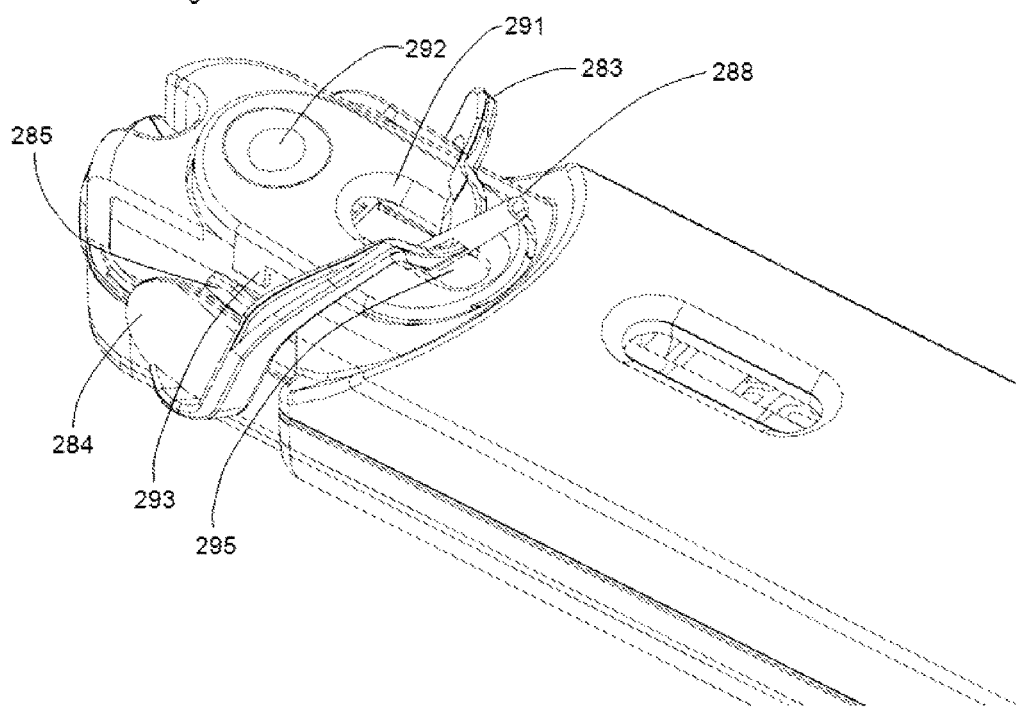
FIG. 45 shows a view similar to FIG. 44, but in a second position.

FIG. 45 illustrates the situation once the blood collection arm 283 has been rotated to the delivery position. The capillary 288 engages the test strip 295 and releases the blood sample. The projection 285 has now rotated to a position where it does not engage foot 293, and so button 292 can be depressed, so as to release the test fluid.

Whilst the illustrated examples provide a single fluid, the present invention could be implemented so that more than one reservoir of fluid is released, either by a single action, or by operating two different buttons or the like. The test may require one or other fluid to be used, depending for example upon some characteristic of the test required or of the individual providing the fluid sample.

The invention claimed is:

1. A disposable composite diagnostic system comprising:
   a support member having at least one housing surface separating an exterior visible from outside the support member and an interior within the support member;
   a membrane penetration element;
   a test material positioned within the interior of the support member;
   a capillary tube extending from an opening outside the support member through the housing surface to an outlet within the interior for discharge onto the test material;
   such that operatively the capillary tube is adapted to take up a bodily fluid after it is released by application of the membrane penetration element and conduct the bodily fluid into contact with the test material;
   an internal reservoir located within the interior of the support member and adapted to contain a physiologically acceptable solution; and
   a solution delivery actuator, the arrangement being such that, actuation of the solution delivery actuator causes the physiologically acceptable solution to be released from the reservoir so that it is brought into contact with the test material after the bodily fluid has contacted the test material.

2. A composite diagnostic system according to claim 1, wherein the solution delivery actuator is adapted to be manually operated.

3. A composite diagnostic system according to claim 1, wherein the solution delivery actuator is operated automatically during use of the system.

4. A composite diagnostic system according to claim 1, wherein the physiologically acceptable solution is a buffer.

5. A composite diagnostic system according to claim 1, wherein the system is adapted to release a controlled amount of fluid by one of displacement, pressure, differential, or capillary forces.

6. A composite diagnostic system according to claim 1, wherein the test material is removable from the support member.

7. A composite diagnostic system as defined in claim 1, wherein the membrane penetration element comprises a lancet.

8. A composite diagnostic system as defined in claim 1, wherein the membrane penetration element comprises a lancing system comprising a lancet tip, the lancet being moveable between a rest position in which the lancet tip is situated within the support member and an actuated position in which the lancet tip extends beyond the exterior of the support member.

9. A composite diagnostic system according to claim 1, wherein the reservoir comprises a sachet containing the physiologically acceptable solution.

10. A composite diagnostic system according to claim 1, further comprising an interface element adapted to allow the system to interface with diagnostic equipment.

11. A composite diagnostic system as defined in claim 10, wherein the interface element is removable and can then engage with diagnostic equipment.

\* \* \* \* \*